(12) United States Patent
Matsuda et al.

(10) Patent No.: US 12,029,303 B2
(45) Date of Patent: Jul. 9, 2024

(54) METHOD FOR PREPARATION OF A COSMETIC KIT

(71) Applicant: SHISEIDO COMPANY, LTD., Tokyo (JP)

(72) Inventors: Takashi Matsuda, Yokohama (JP); Kinya Hosokawa, Yokohama (JP); Chieko Nomizu, Yokohama (JP); Akane Yanagihara, Yokohama (JP); Yuuichi Nukada, Yokohama (JP)

(73) Assignee: SHISEIDO COMPANY, LTD., Tokyo (JP)

( * ) Notice: Subject to any disclaimer, the term of this patent is extended or adjusted under 35 U.S.C. 154(b) by 0 days.

(21) Appl. No.: 18/219,687

(22) Filed: Jul. 9, 2023

(65) Prior Publication Data
US 2023/0354983 A1 Nov. 9, 2023

Related U.S. Application Data

(63) Continuation of application No. 16/766,177, filed as application No. PCT/JP2018/043286 on Nov. 22, 2018, now abandoned.

(51) Int. Cl.
*A45D 33/02* (2006.01)
*A61K 8/00* (2006.01)
*A45D 44/00* (2006.01)

(52) U.S. Cl.
CPC .............. *A45D 33/025* (2013.01); *A61K 8/00* (2013.01); *A45D 2044/007* (2013.01); *A45D 2200/25* (2013.01)

(58) Field of Classification Search
CPC ................ A45D 33/025; A45D 44/005; A45D 2044/007; A45D 2200/25; A61K 8/00
See application file for complete search history.

(56) References Cited

U.S. PATENT DOCUMENTS

| | | | | |
|---|---|---|---|---|
| 5,163,010 A | * | 11/1992 | Klein | B01F 33/8442 366/152.2 |
| 2002/0194021 A1 | * | 12/2002 | Matsumoto | B01F 33/8442 705/2 |

(Continued)

FOREIGN PATENT DOCUMENTS

| | | |
|---|---|---|
| JP | 4-215995 | 8/1992 |
| JP | 2002-284618 | 10/2002 |

(Continued)

OTHER PUBLICATIONS

PCT/JP2018/043286, International Search Report (ISR) and Written Opinion (WO), mailed Feb. 26, 2018, 12 pages—English, 9 pages—Japanese.

*Primary Examiner* — J C Jacyna
(74) *Attorney, Agent, or Firm* — Andrew F. Young; NOLTE LACKENBACH SIEGEL

(57) ABSTRACT

A method for preparing a cosmetic kit provides cosmetics which are customized (personalized) for each user and a cosmetic provision device which uses the kit to supply customized cosmetics. The cosmetic kit includes a plurality of cosmetic bases, and is used for customized cosmetics which are prepared by mixing the plurality of cosmetic bases in accordance with recipe information determined on the basis of user unique information. The method provides a cosmetic kit with a container containing at least two cosmetic bases selected from the plurality of cosmetic bases that is rotated at a prescribed speed, and a new-infrared measurement of the bases in the container is performed at prescribed time intervals, the time (T)required to obtain an nth measurement, in which the rate of change between the absorbance in the nth measurement and the absorbance in the previous ((n−1)th)measurement is 100%±5%, and the rate of change with respect to the absorbance in the follow- (Continued)

ing ((n+1)th) measurement is 100%±5%, is not more than 35 minutes.

6 Claims, 26 Drawing Sheets

(56) References Cited

U.S. PATENT DOCUMENTS

| | | | |
|---|---|---|---|
| 2017/0208921 A1* | 7/2017 | Thiebaut | B01F 33/841 |
| 2019/0046421 A1* | 2/2019 | Yamaki | A61K 8/0254 |

FOREIGN PATENT DOCUMENTS

| | | |
|---|---|---|
| JP | 2003-252721 | 9/2003 |
| JP | 2003-315261 | 11/2003 |
| JP | 3843017 | 11/2006 |

* cited by examiner

FIG.5

USER INFORMATION DATABASE

| USER ID | USER NAME | USER ATTRIBUTE | | | ESTIMATION FORMULA | USED COSMETIC ID | INQUIRY |
|---|---|---|---|---|---|---|---|
| | | GENDER | AGE | ADD | | | |
| U001 | U1 | FEMALE | 28 | TOKYO | f=a1*A+b1*B+c1*C+d1*D | PRO001 | ... |
| U002 | U2 | MALE | 29 | CHIBA | f=a2*A+b2*B+c2*C+d2*D | PRO001 PRO002 | ... |
| ... | ... | ... | ... | ... | ... | ... | ... |

FIG.6

ENVIRONMENT LOG INFORMATION DATABASE (USER ID: U001)

| ENVIORMENT LOG ID | DATE AND TIME | UV EXXPOSURE AMOUNT | TEMPERATURE | HUMIDITY |
|---|---|---|---|---|
| U001 | 2017/5/1 10:00 | 68 | 28 | 48 |
| U002 | 2017/5/1 11:00 | 72 | 32 | 46 |
| . | . | . | . | . |

FIG.7

| ACTION LOG INFORMATION DATABASE (USER ID: U001) | | | | | | |
|---|---|---|---|---|---|---|
| ACTION LOG ID | DATE AND TIME | ACTION | START TIME | END TIME | CALORIE CHANGE | LOCATION |
| ALOG001 | 2017/5/1 8:00 | MEAL | 7:30 | 8:00 | +200 | X1,Y1 |
| ALOG002 | 2017/5/1 9:00 | RUNNING | 8:30 | 9:00 | -500 | X2,Y2 |
| ALOG003 | 2017/5/1 12:00 | MEAL | 11:30 | 12:00 | +400 | X3,Y3 |
| ALOG004 | 2017/5/1 19:00 | MEAL | 18:00 | 19:00 | +1500 | X4,Y4 |
| ALOG005 | 2017/5/2 8:00 | SLEEPING | 22:00 | 8:00 | -1 | X1,Y1 |
| . | . | . | . | . | . | . |

FIG. 8

| PSYCHOSOMATIC LOG INFORMATION DATABASE (USER ID: U001) | | | | | |
|---|---|---|---|---|---|
| PSYCHOSOMATIC LOG ID | DATE AND TIME | PULSE VALUE | ESTROUS CYCLE | STRESS | MINDFULNESS |
| BLOG001 | 2017/5/1 8:00 | 90 | 25 | S1 | M1 |
| BLOG002 | 2017/5/1 9:00 | 60 | 28 | S2 | M2 |
| ⁝ | ⁝ | ⁝ | ⁝ | ⁝ | ⁝ |

FIG.9

SKIN LOG INFORMATION DATABASE
(USER ID: U001)

| SKIN LOG ID | DATE AND TIME | SKIN IMAGE | SKIN COLOR | WATER CONTENT | SEBUM AMOUNT |
|---|---|---|---|---|---|
| SKL001 | 2017/5/1 8:00 | Sk1.jpg | 255,228,196 | WA1 | SE1 |
| SKL002 | 2017/5/1 22:00 | Sk2.jpg | 255,228,197 | WA2 | SE2 |
| SKL003 | 2017/5/2 7:45 | Sk3.jpg | 255,228,198 | WA3 | SE3 |
| SKL004 | 2017/5/2 22:15 | Sk4.jpg | 255,228,199 | WA4 | SE4 |
| . | . | . | . | . | . |

FIG.10

| SKIN EVALUATION LOG INFORMATION DATABASE (USER ID: U001) | | | |
|---|---|---|---|
| SKIN EVALUATOIN LOG ID | DATE AND TIME | SKIN SCORE | |
| | | FIRST SKIN SCORE | SECOND SKIN SCORE |
| EST001 | 2017/5/1 8:00 | 80 | 70 |
| EST002 | 2017/5/1 22:00 | 70 | 90 |
| EST003 | 2017/5/2 7:45 | 90 | 80 |
| EST004 | 2017/5/2 22:15 | 30 | 50 |
| . | . | . | . |

*FIG.11*

| MACHINE INFORMATION DATABASE | | | | | | |
|---|---|---|---|---|---|---|
| MACHINE ID | OWNER USER ID | CARTRIDGE | | | | |
| | | SLOT1 | SLOT2 | SLOT3 | SLOT4 | SLOT5 |
| MA001 | U001 | CA001 80 | CA002 85 | CA003 55 | CA004 70 | CA005 20 |
| MA002 | U002 | CA002 40 | CA002 55 | CA004 55 | CA005 40 | CA006 90 |
| . | . | . | | | | . |

FIG.12

| RECIPE INFORMATION DATABASE | | |
|---|---|---|
| RECIPE ID | USAGE AMOUNT | CONDITION |
| REC001 | CA001=0<br>CA002=0<br>CA003=4<br>CA004=4<br>CA005=2 | 0〜20 |
| REC002 | CA001=0<br>CA002=0<br>CA003=5<br>CA004=1<br>CA005=2 | 20〜40 |
| REC003 | CA001=0<br>CA002=0<br>CA003=10<br>CA004=4<br>CA008=5 | 40〜60 |
| . | . | . |

FIG.18

| RECIPE INFORMATION DATABASE | | | |
|---|---|---|---|
| RECIPE ID | USAGE AMOUNT | SCORE CONDITION | EMOTION CONDITION |
| REC001 | CA001=0<br>CA002=0<br>CA003=4<br>CA004=4<br>CA005=2 | 0~20 | E1 |
| REC002 | CA001=0<br>CA002=0<br>CA003=5<br>CA004=1<br>CA005=2 | 20~40 | E2 |
| REC003 | CA001=0<br>CA002=0<br>CA003=10<br>CA004=4<br>CA008=5 | 40~60 | E3 |
| . | . | . | . |

FIG.20
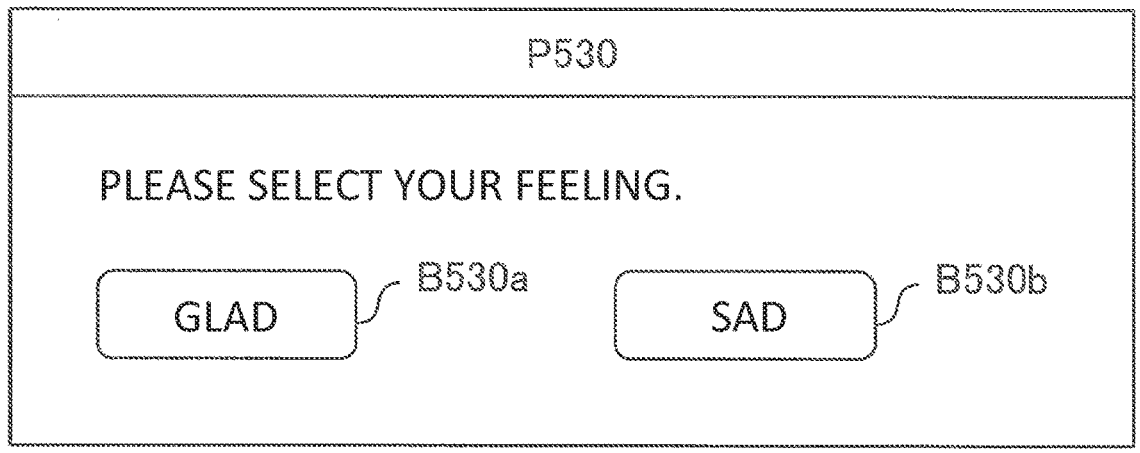
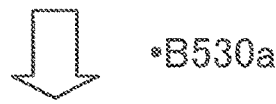
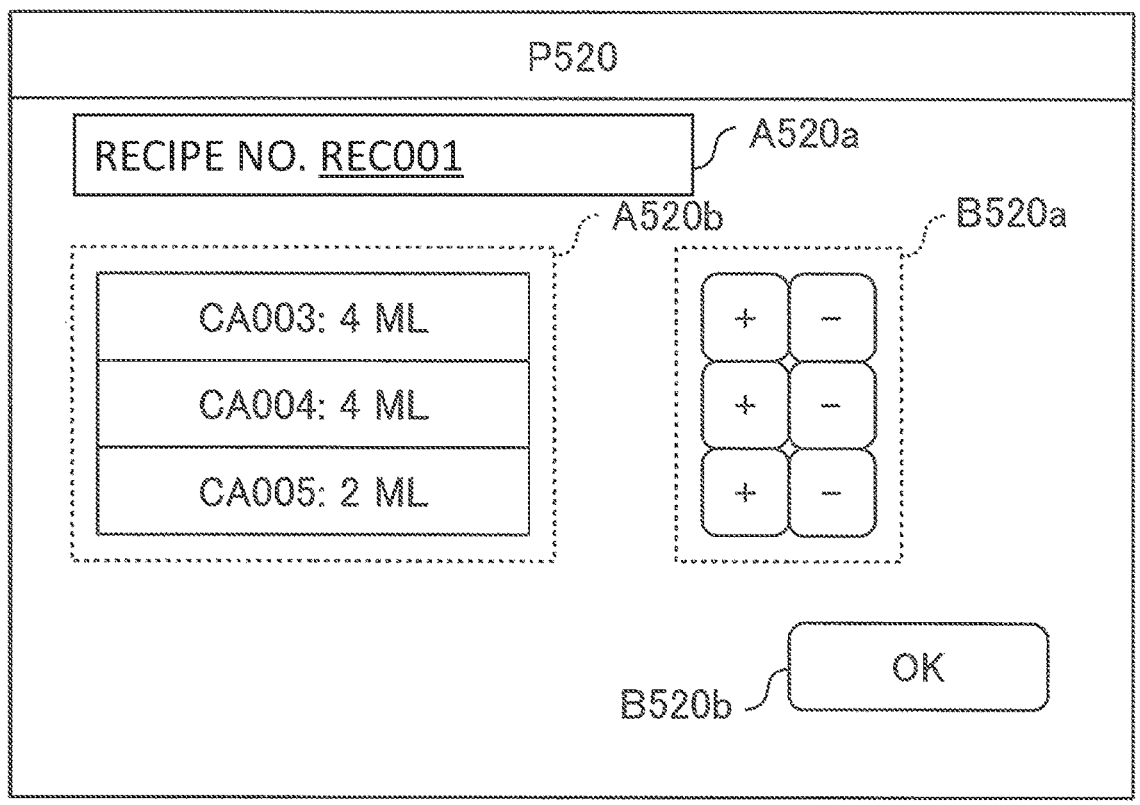
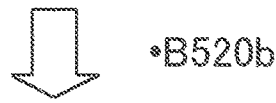

FIG.23

| RECIPE INFORMATION DATABASE | | | | | | | |
|---|---|---|---|---|---|---|---|
| RECIPE ID | USAGE AMOUNT | MIXIER | | | HEATER | | CONDITION |
| | | MIXING SPEED | MIXING ORDER | MIXING TIME | HEATING TEMP | HEATING TIME | |
| REC001 | CA001=0<br>CA002=0<br>CA003=4<br>CA004=4<br>CA005=2 | 2 | 5<br>4<br>3 | 10 | N/A | 0 | 0~20 |
| REC002 | CA001=0<br>CA002=0<br>CA003=5<br>CA004=1<br>CA005=2 | 0 | N/A | 0 | 80 | 3 | 20~40 |
| REC003 | CA001=0<br>CA002=0<br>CA003=10<br>CA004=4<br>CA008=5 | 5 | 3<br>4<br>5 | 5 | 60 | 5 | 40~60 |
| . | . | | | | . | . | |

METHOD FOR PREPARATION OF A COSMETIC KIT

CROSS REFERENCE TO RELATED APPLICATIONS

This application is a continuation of U.S. Ser. No. 16/766,177 filed May 21, 2020, the entire contents of which are incorporated herein by references, which further relates to and claims priority from PCT Ser. No.: PCT/JP2018/043286 filed Nov. 22, 2018, the entire contents of which is incorporated herein by reference which further claims the priority of JP Pat. App. No. 2017-226278 filed Nov. 24, 2017.

FIGURE SELECTED FOR PUBLICATION

FIG. 1

TECHNICAL FIELD

The present invention relates to a method for preparation of a customized cosmetic kit for providing customized cosmetics to an individual who uses the kit.

BACKGROUND OF THE SPECIFICATION

A consumer (user) always has a concern about whether used cosmetics are suitable for the consumer him/herself. In related art, it has been common to purchase cosmetics considered to be suitable for the consumer him/herself while having a consultation in so-called face-to-face selling (point of purchase). In a place of the face-to-face selling simplified measurement of the skin condition ha been performed. However, even if the purchased cosmetics are suitable at the time point of the face-to-face selling, because the preference changes every day and the skin condition changes from moment to moment according to the environment, the psychological condition, and the like, the purchased cosmetics may not always be considered to be suitable cosmetics.

In recent years, it has been suggested that a system which delivers cosmetic ingredients ordered by the consumer and fabricates a specially ordered cosmetic from the ingredients by using a convenient fabrication apparatus which the consumer has (patent document 1). However, only the color of the cosmetic and the type of a product may be selected when the cosmetic is ordered, and only the blending ratio or the like of ingredients is determined according to the selected color and type.

Similar to patent document 1, a system and an apparatus have been suggested which we for fabricating a customized cosmetic according to the skin type of the user in a fabrication apparatus which the user owns (patent document 2). This apparatus only provides a customized cosmetic by mixing a basis selected from five types of cosmetic bases (as a primary category) with an active cosmetic ingredient selected from cosmetic active ingredients (as a secondary category).

In other words, in the systems in related art, even if m ingredient reflecting the skin condition at the time point of the order is blended, the cosmetic does not correspond to the user him/herself or the change in the environment, and the cosmetic may hardly be considered to be a real customized cosmetic (personalized cosmetic) in the true sense as the cosmetic suitable for the user him/herself on the very day.

CITATION LIST

Patent Document

Patent Document 1: JP 3843017 B
Patent Document 2: JP 2017-510389 A

SUMMARY OF INVENTION

Technical Problem

Accordingly, an object of the present subject matter is to provide a cosmetic kit suitable for providing a cosmetic suitable for a user on the very day and at the very time ("customized cosmetic" in the true sense) in consideration of user-unique factors that are considered to possibly affect the skin condition, for example, an environment where the user spends time, a user's action, and a use's psychosomatic state.

Solution to Problem

To solve the above problem, the inventors have conducted intensive studies, thus found that mixability of each base is very important when each base for preparing a customized cosmetic is caused to have an original feature, the types and blending amounts of bases configuring the customized cosmetic suitable for a user on the very day and at the very time are determined based on user-unique information, and the base is dispensed to the user via a cosmetic dispenser, and completed de present embodiment.

Accordingly, the present embodiment provides a cosmetic kit including a plurality of cosmetic bases, the cosmetic kit being used for a customized cosmetic prepared by mixing the plurality of cosmetic bases in accordance with recipe information determined based on user-unique information, in which when a container containing at least two types of cosmetic bases selected from the plurality of cosmetic bases is rotated at a predetermined speed and new-infrared ray measurements of the bases in the container are conducted at predetermined time intervals, time (T) required until an nth measurement is within 35 minutes, a change ratio of $100\%\pm5\%$ between absorbance in the nth measurement and absorbance in a previous (n−1)th measurement and a change ratio of $100\%\pm5\%$ between the absorbance in the nth measurement and absorbance in a next (n+1)th measurement being achieved for the first time by the nth measurement.

Advantageous Effects of Invention

In a cosmetic kit of the present embodiment, because a plurality of cosmetic bases included in the kit have original features and we prepared to be mixable with each other, a user may, easily ad without stress, mix cosmetic bases dispensed according to recipe information based on user-unique information and obtain a customized cosmetic. Because a prescription of each cosmetic base is determined based on the user-unique information and the like, a customized cosmetic in the true sense may efficiently and conveniently be provided to the user, the customized cosmetic being flexibly variable according to the users condition on the very day and at the very time, and a concern of the user about cosmetics may be resolved.

BRIEF DESCRIPTION OF DRAWINGS

FIG. 5 is a diagram showing a data structure of a user information database according to the embodiment of FIG. 4.

FIG. 6 is a diagram showing a data structure of a environment log information database according to the embodiment of FIG. 4.

FIG. 7 is a diagram showing a data structure of n action log information database according to the embodiment of FIG. 4.

FIG. 8 is a diagram showing a data structure of a psychosomatic log information database according to the embodiment of FIG. 4.

FIG. 9 is a diagram showing a data structure of a skin log information database of n embodiment.

FIG. 10 is a diagram showing a data structure of a skin evaluation log information database of a embodiment.

FIG. 11 is a diagram showing a data structure of a machine information database of a embodiment.

FIG. 12 is a diagram showing a data structure of a recipe information database of an embodiment.

FIG. 18 is a diagram illustrating a data structure of a recipe information database according to a first variation.

FIG. 20 is a diagram of an example of screen displayed in the information processing of FIG. 19.

FIG. 23 is a diagram illustrating a data structure of a recipe (formulation)information database according to a third variation.

BRIEF DESCRIPTION OF THE EMBODIMENTS

Figure 1:
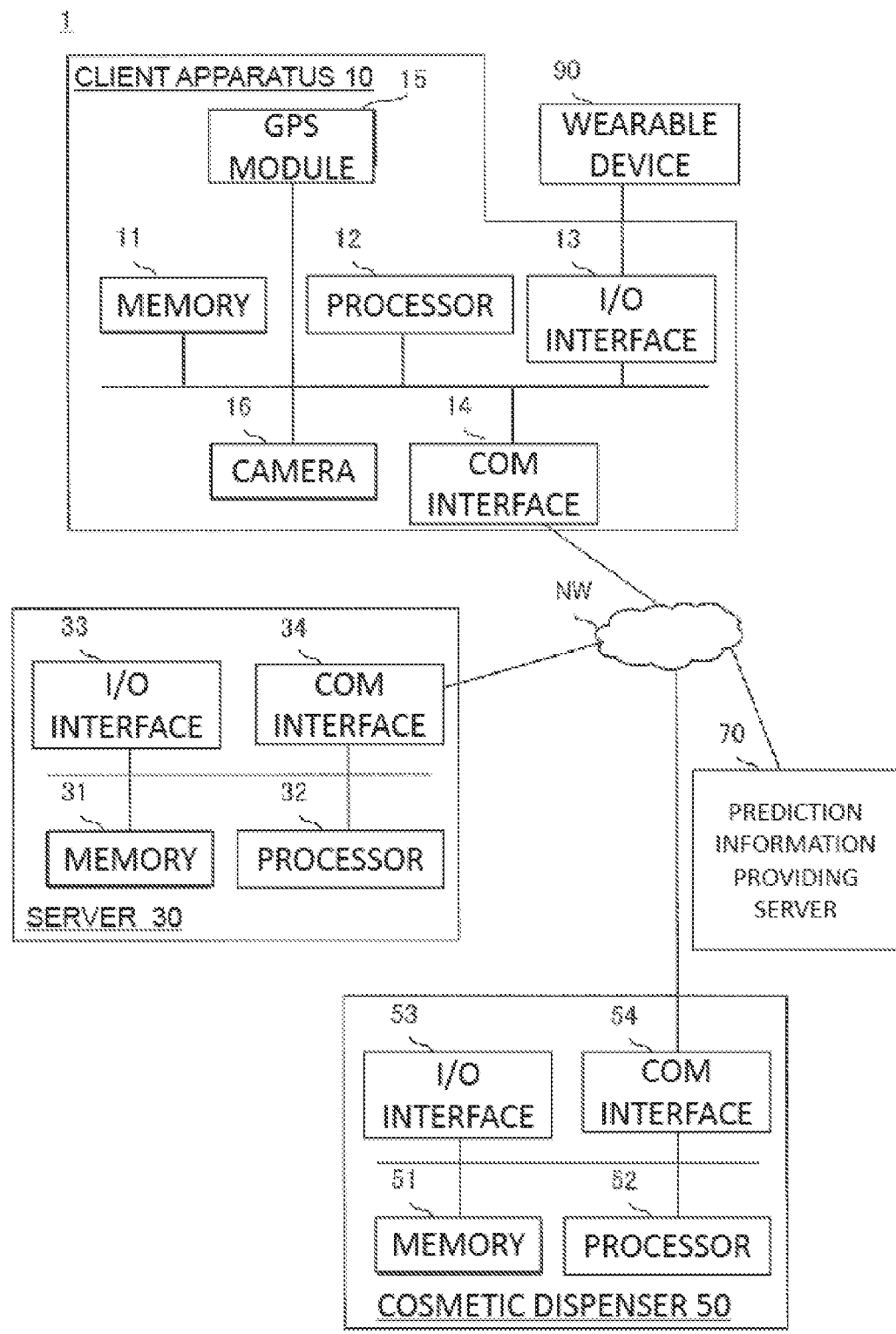
FIG. 1 is a block diagram showing a configuration of one aspect of an information processing system including a cosmetic dispenser and an information processing apparatus that are suitable for use of a cosmetic kit according to the present invention.

A cosmetic kit of the present invention is particularly suitable, for example, for use with a cosmetic dispenser including: a plurality of cartridge slots configured to hold cartridges containing cosmetic bases, each cartridge detachable with each cartridge slot; and a dispenser configured to dispense the cosmetic base contained in the cartridge held by each of the plurality of cartridge slots according to recipe information indicating a usage amount or the like of each cosmetic base, the usage amount determined based on user-unique information.

Note that "cosmetic base" (hereinafter simply referred to as "base" also) in this specification means a preparation (composition) that includes a cosmetic ingredient and may individually be used as a cosmetic.

The cosmetic dispenser is preferably connected with and capable of communicating with an information processing apparatus capable of performing information processing based on the user-unique information, and de recipe information is preferably transmitted from the information processing apparatus. A detailed description will be made in the following.

An information processing apparatus preferably used in the present invention includes: a retrieve module configured to retrieve the user-unique information unique to the user, the user-unique information including at least one of user attribute information related to the use's attributes, environmental information related to the user's environment, action information related to the use's action, psychosomatic information related to the user's psychosomatic, skin information related to the ues's skin, and information related to cosmetics which the user has used; a selection module configured to select the recipe information based on the user-unique information among a plurality of recipe information; and a transmission module configured to transmit the selected recipe information to the cosmetic dispenser.

A detailed description will hereinafter be made with reference to drawings. However, in the drawings for describing the embodiments, the same components are denoted by the same reference sign in principle, and the repetitive description thereof is omitted.

(1) Configuration of Information Processing System

The configuration of the information processing system including the cosmetic dispenser and the information processing apparatus will be described. FIG. 1 is a block diagram showing the configuration of the information processing system according to the present embodiment.

As shown in FIG. 1, the information processing system 1 includes a client apparatus 10, a server 30, a cosmetic dispenser 50, a prediction information providing server 70, and a wearable device 90. The client apparatus 10, the server 30, the cosmetic dispenser 50, mid the prediction information providing server 70 are connected via a network (for example, m internet or an intranet) NW.

The client apparatus 10 is example of m information processing apparatus that transmits a request to the server 30. The client apparatus 10 is, for example, a smartphone, a tablet device, or a personal computer.

The server 30 is m example of an information processing apparatus that provides a response corresponding to a predetermined request to the client apparatus 10 and the cosmetic dispenser 50. The server 30 is, for example, a web server.

The cosmetic dispenser 50 is configured to provide cosmetics based on information transmitted from the server 30.

The prediction information providing server 70 is an example of an information processing apparatus that provides prediction information indicating future prediction. For example, the prediction information providing server 70 provides the following information:
environment prediction information indicating prediction of future environment (for example, weather prediction of a place where the user lives);

action prediction information indicating prediction of future user's action (for example, a schedule arbitrarily input by the user); and psychosomatic prediction information indicating the prediction of the use's psychosomatic (for example, the prediction date of the sexual cycle arbitrarily input by the user).

The wearable device 90 includes at least one of environment log information (FIG. 6 described later), action log information (FIG. 7 described later), and psychosomatic log information (FIG. 8 described later).

(1-1) Configuration of Client Apparatus

As shown in FIG. 1, the client apparatus 10 includes a mommy 11, a processor 12, an input and output (hereinafter, referred to as "I/O") interface 13, a communication interface 14, a GPS module 15, and a camera 16.

The memory 11 is configured to store a program and data. The memory 11 is, for example, a combination of a ROM (read only memory), a RAM (random access memory), and a storage (for example, a flash memory or a hard disk).

The program includes, for example, the following programs:
OS (Operating System)program; and
program of application for executing information processing (for example, a cosmetic dispense application linked to the cosmetic dispenser 50).

The data includes, for example, the following data:
database referred to in information processing; and
data obtained by executing information processing (that is, execution result of information processing).

The processor 12 is configured to activate a program stored in the memory 11 to implement the functions of the client apparatus 10. The processor 12 is n example of a computer.

The I/O interface 13 is configured to acquire a user instruction from n input device connected to the client apparatus 10, acquire information from the wearable device 90, and output information to e output device connected to the client apparatus 10. The input device is, for example, a keyboard, a pointing device, a touch panel, or a combination thereof. The output device is, for example, a display.

The communication interface 14 is configured to control communication between the client apparatus 10 and the server 30.

The GPS module 15 is configured to acquire location information of the client apparatus 10 by communicating with a GPS (Global Positioning System) satellite.

The camera 16 is configured to capture n image. The camera 16 is, for example, a CMOS (Complementary Metal Oxide Semiconductor) camera.

(1-2) Server Configuration

As shown in FIG. 1, the server 30 includes a memory 31, a processor 32, and a communication interface 34.

The memory 31 is configured to store a program and data. The memory 31 is, for example, a combination of ROM, RAM, and storage (for example, flash memory or hard disk).

The program includes, for example, the following programs:
OS program; and
program of application for executing information processing.

The data includes, for example, the following data
database referred to in information processing; and
execution result of information processing.

The processor 32 is configured to activate a program stored in the memory 31 to implement the functions of the server 30. The processor 32 is an example of a computer.

The I/O interface 33 is configured to acquire a user instruction from an input device connected to the server 30 and output information to n output device connected to the server 30. The input device is, for example, a keyboard, a pointing device, a touch panel, or a combination thereof. The output device is, for example, a display.

The communication interface 34 is configured to control communication between the server 30 and the client apparatus 10.

(1-3) Configuration of Cosmetic Dispenser

As shown in FIG. 1, the cosmetic dispenser 50 includes a memory 51, a processor 52, an I/O interface 53, and a communication interface 54.

The memory 51 is configured to store a program and data. The memory 51 is, for example, a combination of ROM, RAM, and storage (for example, flash memory or hard disk).

The program includes, for example, the following programs:
OS program;
firmware program for controlling the cosmetic dispenser 50;
OS program;
program of application for executing information processing.

The data includes, for example, the following data:
database referred to in information processing; and
data obtained by executing information processing (that is, execution result of information processing).

The processor 52 is configured to activate a program stored in the memory 51 to realize the functions of the cosmetic dispenser 50. The processor 52 is a example of a computer.

The I/O interface 53 is configured to receive a user instruction from the input device of the cosmetic dispenser 50 or the client apparatus 10, and output information to the output device of the cosmetic dispenser 50. The input device is, for example, a touch panel. The output device is, for example, a display.

The communication interface 54 is configured to control communication between the cosmetic dispenser 50 and the server 30.

The structure and configuration of one aspect of the cosmetic dispenser usable in the embodiment of FIG. 1 will be described.

Figure 2A:
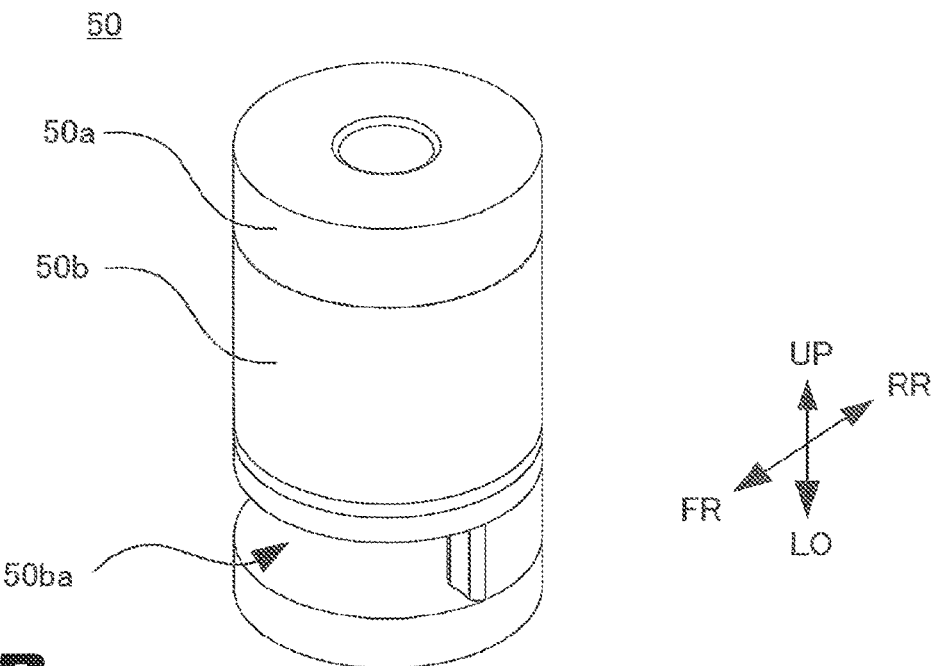
FIG. 2A, 2B are diagrams showing a structure of one aspect of the cosmetic dispenser of FIG. 1.
Figure 2B:
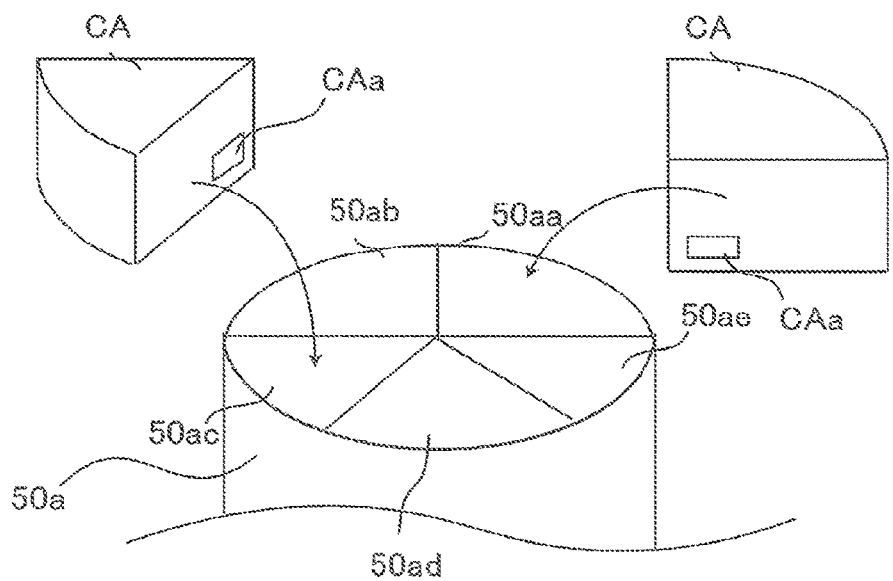
Figure 3:
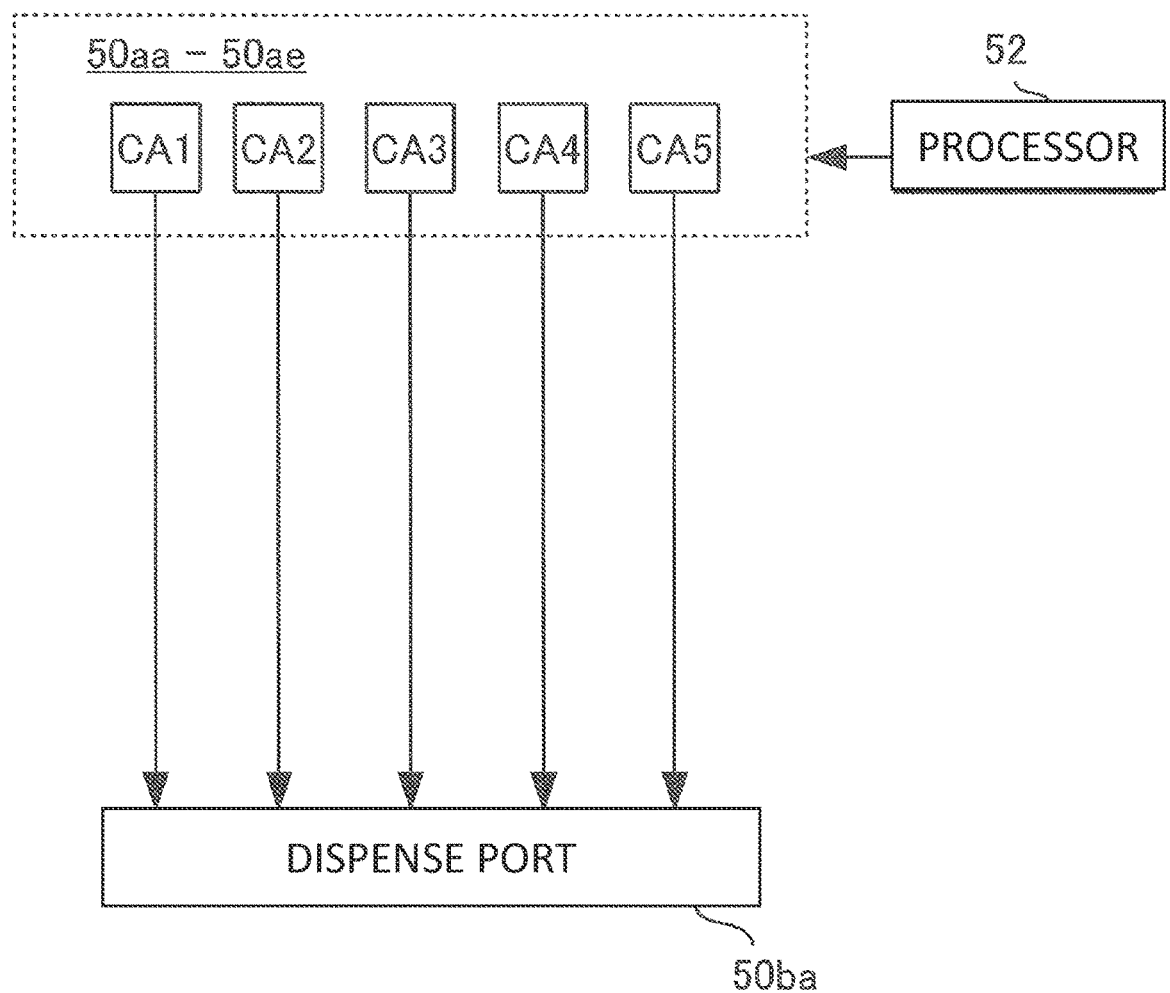
FIG. 3 is a diagram showing a configuration of one aspect of the cosmetic dispenser of FIG. 1.

FIG. 2A, 2B are diagrams showing the structure of a form of the cosmetic dispenser. FIG. 3 is a schematic diagram showing an example of the configuration of the cosmetic dispenser of FIG. 2.

As shown in FIG. 2A, the cosmetic dispenser 50 includes an upper part 50a and a lower part 50b. A dispense port 50ba is disposed in the lower part 50b. The dispense port Sob opens toward the front FR.

As shown in FIG. 2B, a plurality of cartridge slots 50a to 50ae are disposed inside the upper part 5s. A cartridge CA is detachably held in each of the cartridge slots 50aa to 50ae.

Each cartridge CA contains a cosmetic base (for example, liquid). The cosmetic base contained in each cartridge CA may be used individually and may be nixed with the cosmetic bases contained in other cartridges CA.

An IC chip CAa is disposed on the side surface of each cartridge CA. The IC chip CAa stores information related to the cartridge CA (hereinafter referred to as "cartridge information").

The cartridge information includes, for example, the following information:
- cartridge ID for identifying the cartridge;
- remaining amount value of the cosmetic bases contained in the cartridge; and
- information indicating the cosmetic bases contained in the cartridge.

As shown in FIG. 3, each of the cartridge slots 50aa to 50ae holds the cartridges CA1 to CA5. Cosmetic base different from each other or the same cosmetic bases are contained in the cartridges CA1 to CA5.

The processor 52 controls the cartridges CA1 to CA5 to dispense the cosmetic bases contained in the cartridges CA1 to CA5 from the dispense port 50ba.

(2) Outline of Customized Cosmetic Dispensing Method

Figure 4:
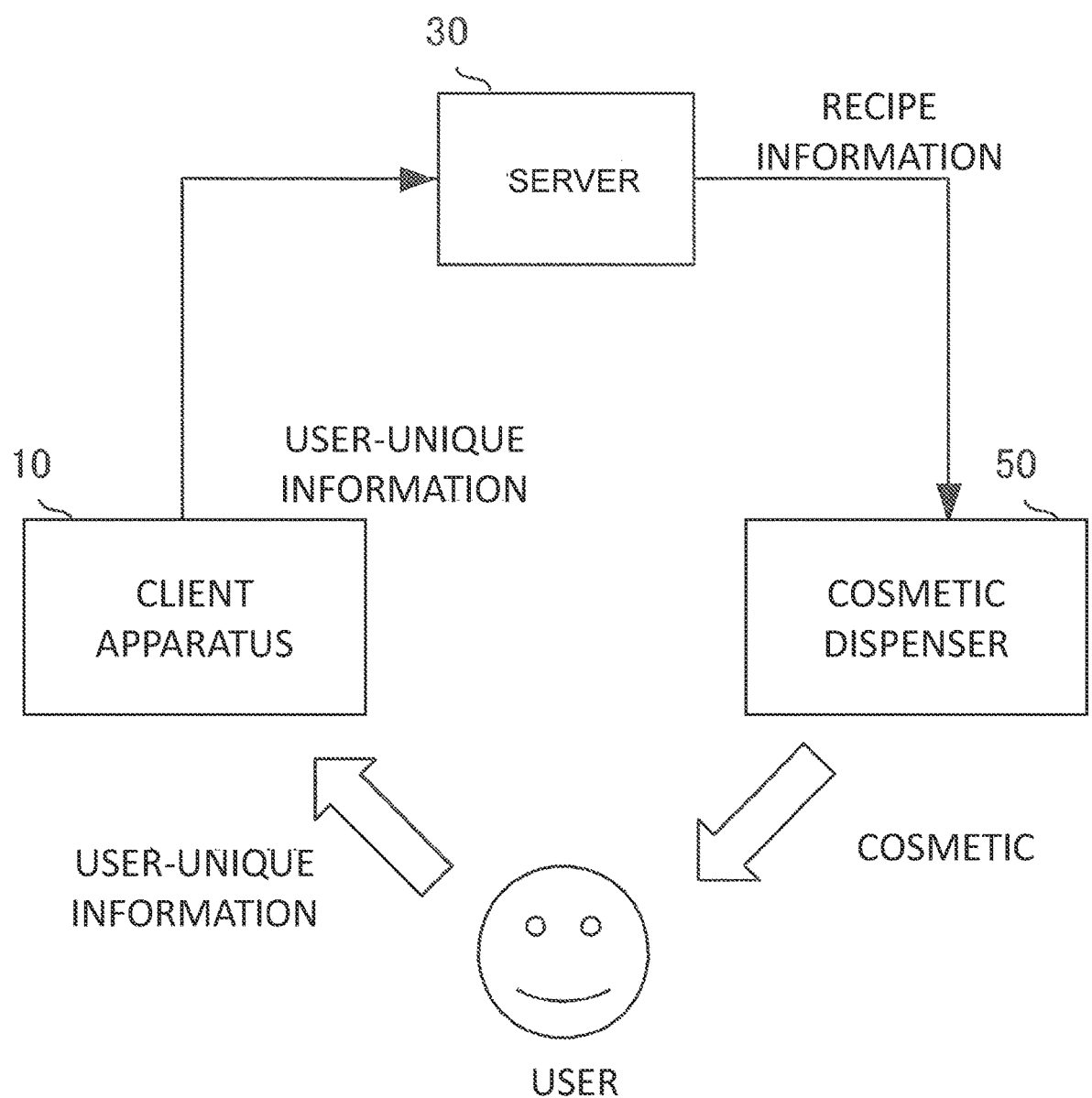
FIG. 4 is a schematic diagram of a embodiment of a dispensing method of customized cosmetics using the information processing system of FIG. 1.

FIG. 4 is a schematic diagram showing an embodiment of a dispensing method of customized cosmetics by using the information processing system of FIG. 1.

As shown in FIG. 4, in the present embodiment, a user (for example, a consumer of cosmetics) uses the client apparatus 10 and the cosmetic dispenser 50.

The client apparatus 10 acquires information unique to the user (hereinafter referred to as "user-unique information") from the user. The client apparatus 10 transmits the acquired user-unique information to the server 30.

The user-unique information includes user log information and prediction information.

The user log information is information indicating at least one history of the user's past environmental information, action information, psychosomatic information, skin information, and skin evaluation information.

The prediction information is information indicating at least one prediction of the user's future environment, action, and psychosomatic.

The server 30 selects recipe information to be transmitted to the cosmetic dispenser 50 among a plurality of recipe information based on the user-unique information transmitted from the client apparatus 10. The server 30 transmits the selected recipe information to the cosmetic dispenser 50.

The cosmetic dispenser 50 dispense cosmetic bases from the dispense port 50ba based on the recipe information transmitted from the server 30. Recipe information is based on user-unique information. That is, the cosmetics configured with cosmetic bases dispensed to the user we customized according to the factors unique to the user.

(3) Database

The database of the present embodiment will be described. The following database is stored in the memory 31.

(3-1) User Information Database

The user information database of the present embodiment will be described. FIG. 5 is a diagram illustrating an example of a data structure of the user information database according to the present embodiment.

The user information database shown in FIG. 5 stores information related to users (hereinafter referred to as "user information").

The user information database includes a "user ID" field, a "user name" field, a "user attribute" fid, an "estimation formula" fid, a "used cosmetic ID" field, and an "inquiry" field. Each field is associated with each other.

The "user ID" field stores a user ID for identifying the user.

The "user name" field stores information (for example, text) indicating the username.

The "user attribute" field stores information related to user attributes (hereinafter referred to as "user attribute information"). The user attribute information is information arbitrarily determined by the user. The "user attribute" field includes a "gender" field, an "age" field, and an "address" field. The "gender" field stores information indicating the gender of the user. The "age" field stores information indicating the age of the user. The "address" field stores information indicating the address of the user.

The "estimation formula" field stores an estimation formula (equation I) for estimating the skin condition of the user. The estimation formula includes a coefficient for each factor that affects the use's skin.

$$f = a \times A + b \times B + c \times C + d \times D \qquad \text{(Equation I)}$$

f . . . Score indicating the estimation result of skin condition (hereinafter referred to as "skin score");
a . . . Environmental coefficient;
A . . . Environmental information;
b . . . Action coefficient;
B . . . Action information;
c . . . Psychosomatic coefficient;
C . . . Psychosomatic information;
d . . . Skin coefficient; and
D . . . Skin information.

An estimation formula is prepared for each user's skin condition index (hereinafter referred to as "skin index"). That is, the coefficient included in the estimation formula is different for each skin index. The skin index is, for example, at least one of the following:
- moisture content of the stratum corneum;
- skin texture, skin color;
- dry skin, skin smoothness;
- ski transparency;
- degree of skin whitening;
- skin roughness;
- degree of skin inflammation; and
- degree of skin wrinkles.

The "used cosmetic ID" field stores a cosmetic ID for identifying the cosmetic which the user has used.

The "inquiry" field stores information indicating the user's answer to the question related to the use's skin.

(3-2) Environmental Log Information Database

FIG. 6 is a diagram illustrating an example of a data structure of the environment log information database according to the present embodiment.

The environment log information database of FIG. 6 stores information (hereinafter referred to as "environment log information") indicating a log of environment information related to the environment spent by the user, the environment log information is information acquired from the wearable device 90.

The environmental log information database includes n "environment log ID" field, a "date and time" field, an "UV exposure amount" field, a "temperature" field, and a "humidity" field. Each field is associated with each other. The environment log information database is associated with the user ID.

The "environment log ID" field stores an environment log ID for identifying environment information constituting the environment log information.

The "date and time" field storm information indicating the date and time when the environment information was acquired.

The "UV exposure amount" field stores information indicating the amount of ultraviolet rays that the user has taken (hereinafter referred to as "UV exposure amount").

The "temperature" field stores information indicating the temperature of the environment spent by the user.

The "humidity" field stores information indicating the humidity of the environment spent by the user.

(3-3) Action Log Information Database

FIG. 7 is a diagram illustrating n example of a data structure of the action log information database according to the present embodiment.

The action log information database shown in FIG. 7 stores information (hereinafter referred to as "action log information") indicating a history of action information relating to users action. The action log information is information acquired from the wearable device 90, information determined according to a user instruction (for example, a user's answer to a questionnaire), or a combination thereof.

The action log information database includes an "action log ID" field, a "date and time" field, an "action" field, a "start time" field, an "end time" field, a "calorie change" field, and a "location" field. Each field is associated with each other. The action log information database is associated with the user ID.

The "action log ID" field stores an action log ID for identifying action information constituting the action log information.

The "date and time" field stores information indicating the date and time when the action information is acquired.

The "action" field stores information related to the user's action. The user's action includes at least one of the following
- meals (for example, the contents of meals);
- exercise (for example, the event of exercise); and
- sleep (for example, the number of wake-ups during sleep).

The "start time" field stores information indicating the start time of the action.

The "end time" field stores information indicating the end time of the action.

The "calorie change" field stores information indicating calorie intake or calorie consumption (a example of energy consumption) corresponding to the action.

The "location" field stores the location information acquired by the GPS module 15.

(3-4) Psychosomatic Log Information Database

FIG. 8 is a diagram showing an example of a data structure of the psychosomatic log information database of the present embodiment.

The psychosomatic log information database shown in FIG. 8 stores information indicating the history of psychosomatic information related to the users psychosomatic (hereinafter referred to as "psychosomatic information"). The psychosomatic log information is information determined according to information acquired from the wearable device 90, a user instruction (for example, a use's answer to an inquiry (hereinafter referred to as "inquiry result")), or a combination thereof.

The psychosomatic log information database includes a "psychosomatic log ID" field, a "date and time" field, a "pulse value" field, a "sexual cycle" field, a "stress" field, and a "mindfulness" field. Each field is associated with each other. The psychosomatic log information database is associated with the user ID.

The "psychosomatic log ID" field stores a psychosomatic log ID for identifying psychosomatic information constituting the psychosomatic log information.

The "date and time" field stores information indicating the date and time when psychosomatic information is acquired.

The "pulse value" field stores the pulse value of the user. The pulse value is information acquired from the wearable device 90, for example.

The "sexual cycle" field stores information indicating a sexual cycle (an example of hormone balance information).

The "stress" field stores stress information indicating an index of stress. The stress information indicates, for example, the intensity of stress the factor of stress, the type of stress, or a combination thereof, the stress information is determined by the pulse value, the sexual cycle, the inquiry result, or a combination thereof.

The "mindfulness" field stores mindfulness information indicating a use's mindfulness index. Mindfulness information is determined by the pulse value, the sexual cycle, the inquiry result, or a combination thereof.

(3-5) Skin Log Information Database

FIG. 9 is a diagram showing an example of a data structure of the skin log information database of the present embodiment.

The skin log information database in FIG. 9 stores information (hereinafter referred to as "skin log information") indicating a history of skin information related to the user's skin.

The skin log information database includes a "skin log ID" field, a "date and time" field, a "skin image" field, a "skin color" field, a "water content" field, and a "sebum amount" field. Each field is associated with each other. The skin log information database is associated with the user ID.

The "skin log ID" field stores a skin log ID for identifying skin log information.

The "date and time" field stores information indicating the date and time when the skin information is acquired.

The "skin image" field stores image data of the ues skin image.

The "skin color" field stores information (for example, RGB values)indicating the skin color estimated from the user's skin image.

The "water content" field stores information indicating a water content index estimated from the user's skin image.

The "sebum amount" field stores information indicating an index of the sebum amount estimated from the user's skin image.

(3-6) Skin Evaluation Log Information Database

FIG. 10 is a diagram illustrating an example of a data structure of the skin evaluation log information database according to the present embodiment.

The skin evaluation log information database of FIG. 10 stores information (hereinafter referred to as "skin evaluation log information") indicating a history of qualitative evaluation (hereinafter referred to as "skin evaluation") related to the skin condition.

The skin evaluation log information database includes a "skin evaluation log ID" field, a "date and time" field, and a "skin score" field. Each field is associated with each other. The skin evaluation log information database is associated with the user ID.

The "skin evaluation log ID" field stores a skin evaluation log ID for identifying the skin evaluation constituting the skin evaluation log information.

The "date and time" field stores information indicating the date and time when the skin evaluation is generated.

The "skin score" field stores a skin score acquired by applying user log information (at least one of environment log information, action log information, psychosomatic log information, and skin log information) to the estimation formula. The "skin score" field includes a "first skin score" field and a "second skin score" field.

The "first skin score" field stores a first skin score (an example of a first skin index). The first skin score indicates a current skin state estimated from user log information (for example, when user log information is acquired).

The "second skin score" field stores a second skin score (n example of a second skin index), the second skin score indicates the skin state of the future estimated from user log information and prediction information (for example, one week after the day when user log information was acquired).

(3-7) Machine Information Database

FIG. 11 is a diagram illustrating n example of a data structure of the machine information database according to the present embodiment.

The machine information database of FIG. 11 stores information related to the cosmetic dispenser 50 (hereinafter referred to as "machine information").

The machine information database includes a "machine ID" field, an "owner user ID" field, and a "cartridge" field. Each field is associated with each other.

The "machine ID" field stores a machine ID for identifying the cosmetic dispenser 50. The information in the "machine ID" field is, for example, a serial number assigned in advance to the cosmetic dispenser 50.

The "owner user ID" field stores the user ID of the user who uses the cosmetic dispenser 50.

we "cartridge" field includes "slot 1" to "slot 5" fields.

The "slot 1" to "slot 5" fields store cartridge information relating to the cartridges CA1 to CA5 held in the cartridge slots 50aa to 50ae, respectively. The cartridge information includes a cartridge ID for identifying the cartridge CA, and a remaining amount value of the cosmetic base contained in die cartridge CA, and information indicating the cosmetic base contained in the cartridge CA.

(3-8) Recipe Information Database

FIG. 12 is a diagram illustrating an example of a data structure of the recipe information database according to the present embodiment.

Recipe information database of FIG. 12 stores the recipe information. The recipe information indicates a method for customizing cosmetics.

The recipe information database includes a "recipe ID" field, a "usage amount" field, and a "condition" field. Each field is associated with each other.

The "recipe ID" field stores a recipe ID for identifying recipe information. Information in the "recipe ID" field is determined by the server 30.

The "usage amount" field stores information indicating the usage amount of each cosmetic base.

The "condition" field stores information indicating the range of the skin score as a reference when selecting recipe information.

(4) Information Processing

Figure 13:
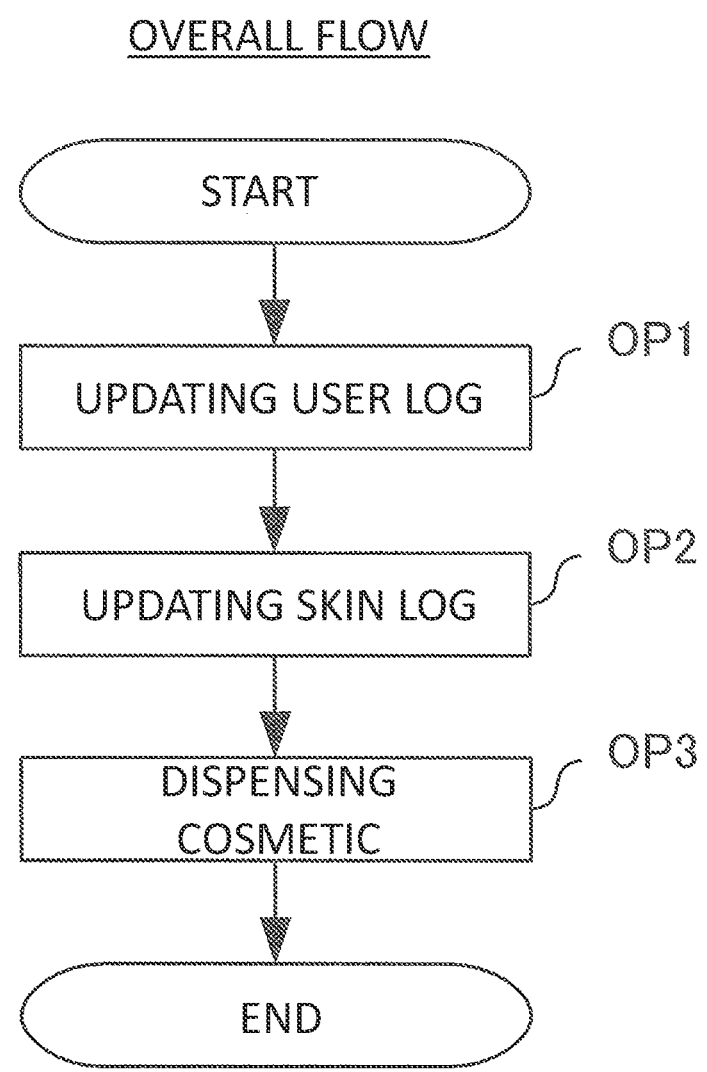
FIG. 13 is a diagram illustrating an overall flow of information process of an embodiment.

FIG. 13 is a diagram illustrating an overall flow of information processing according to the present embodiment.

As shown in FIG. 13, the information processing according to the present embodiment includes updating the user log (OP1), updating the skin log (OP2), and dispensing cosmetics (OP3).

(4-1) User Log Update Processing

Figure 14:
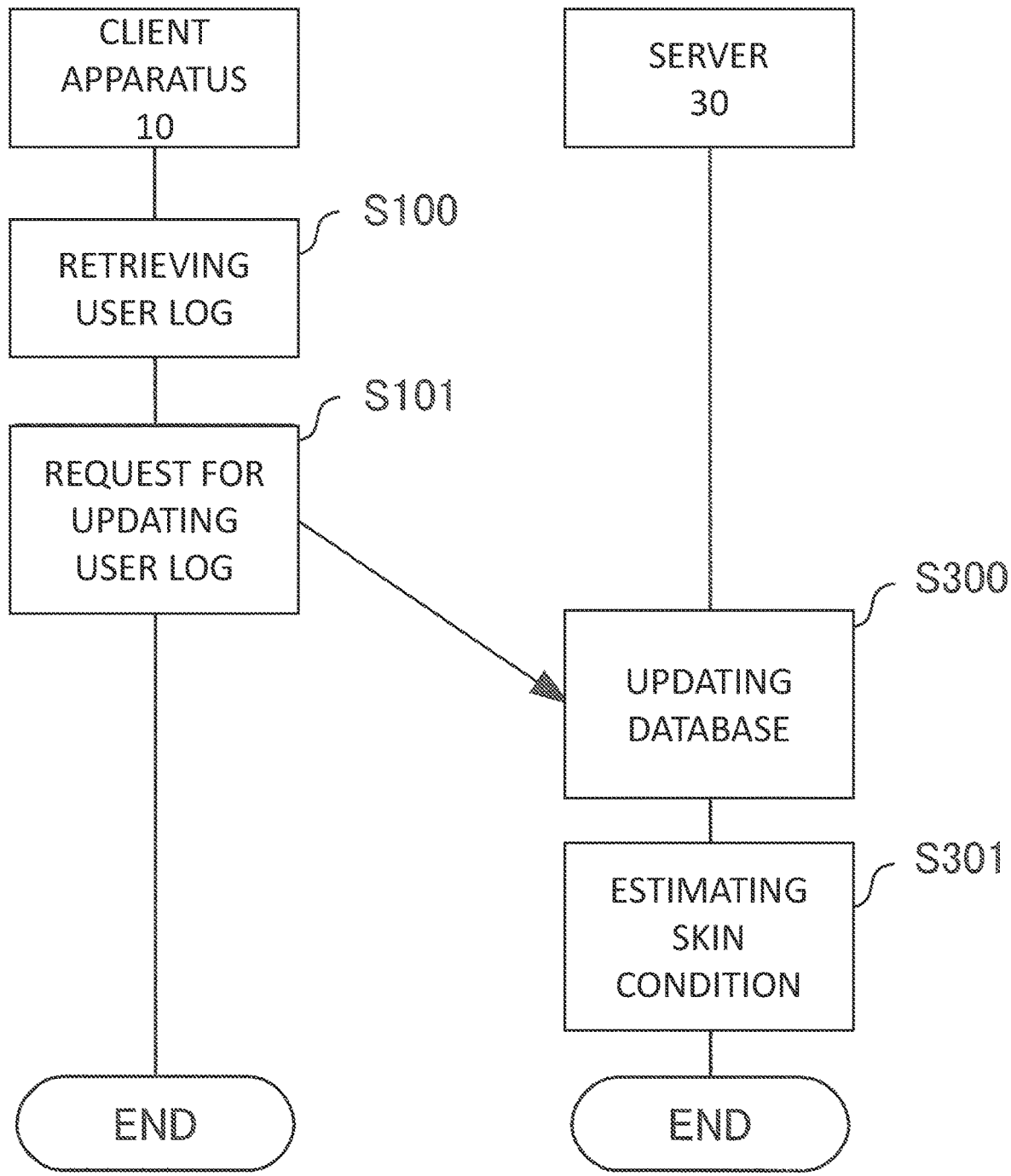
FIG. 14 is a flowchart of process for updating user log of an embodiment.

FIG. 14 is a flowchart of process for updating user log according to the present embodiment.

Of the steps in FIG. 14, the step executed by the client apparatus 10 is executed as a function of the cosmetic dispense application.

As shown in FIG. 14, the client apparatus 10 executes retrieving user log (S100).

Specifically, the processor 12 acquires user log information (at least one of environment log information, action log information, and psychosomatic log information) from the wearable device 90 via the I/O interface 13.

After step S100, the client apparatus 10 executes a user log update request (S101).

Specifically, the processor 12 transmits user log update request data to the server 30.

The user log update request data includes the following information:
user D
information indicating date and time of execution of step S101; and
User log information acquired in step S100.

After step S101, the server 30 executes updating database (S300) based on user log update request data.

As a first example, when the user log update request data includes environment log information, the processor 32 adds a new record into the environment log information database (FIG. 6) associated with the user ID included in the user log update request data transmitted in step SOI.

The following information is stored in each field of the new record:
in the "environment log ID" field, a new environment log ID is stored;
in the "date and time" field, information indicating the execution date and time of step S101 included in the user log update request data is stored, and
in the "UV exposure amount" field, the "temperature" field, and the "humidity" field, environment information included in the user log update request data is stored.

As a second example, when the user log update request data includes the action log information, the processor 32 adds a new record into the action log information database (FIG. 7) associated with the user ID included in the user log update request data transmitted in step S101.

the following information is stored in each field of the new record:
in the "action log ID" field, a new action log ID is stored;
in the "date and time" field, information indicating the execution date and time of step S101 included in the user log update request data is stored; and
in the "action" field, the "start time" field, the "end time" field, the "calorie change" field, and the "location" field, action information included in the user log update request data is stored.

As a third example, when the user log update request data includes psychosomatic log information, the processor 32 adds a new record into the psychosomatic log information database (FIG. 8) associated with the user ID included in the user log update request data transmitted in step S101.

The following information is stored in each field of the new record.
in the "psychosomatic log 1D" field, a new psychosomatic log ID is stored;
in the "date ad time" field, information indicating the execution date and time of step S101 included in the user log update request data is stored; and
in the "pulse value" field, the "sexual cycle" field, the "stress" field, and the "mindfulness" field, psychosomatic information included in the user log update request data is stored.

Thereby, the user log information is updated.

After step S300, the server 30 executes estimating skin condition (S301).

Specifically, the processor 32 refers to the user information database (FIG. 5) aid specifies an estimation formula associated with the user ID included in the user log update request data.

The processor 32 calculates the skin score based on the user log information by applying the user log information updated in step S300 to the specified estimation formula.

The processor 32 stores information indicating the calculated skin score in the "first skin score" field of the skin evaluation log information database (FIG. 10) associated with the user ID.

(4-2) Skin Log Update Processing

Figure 15:
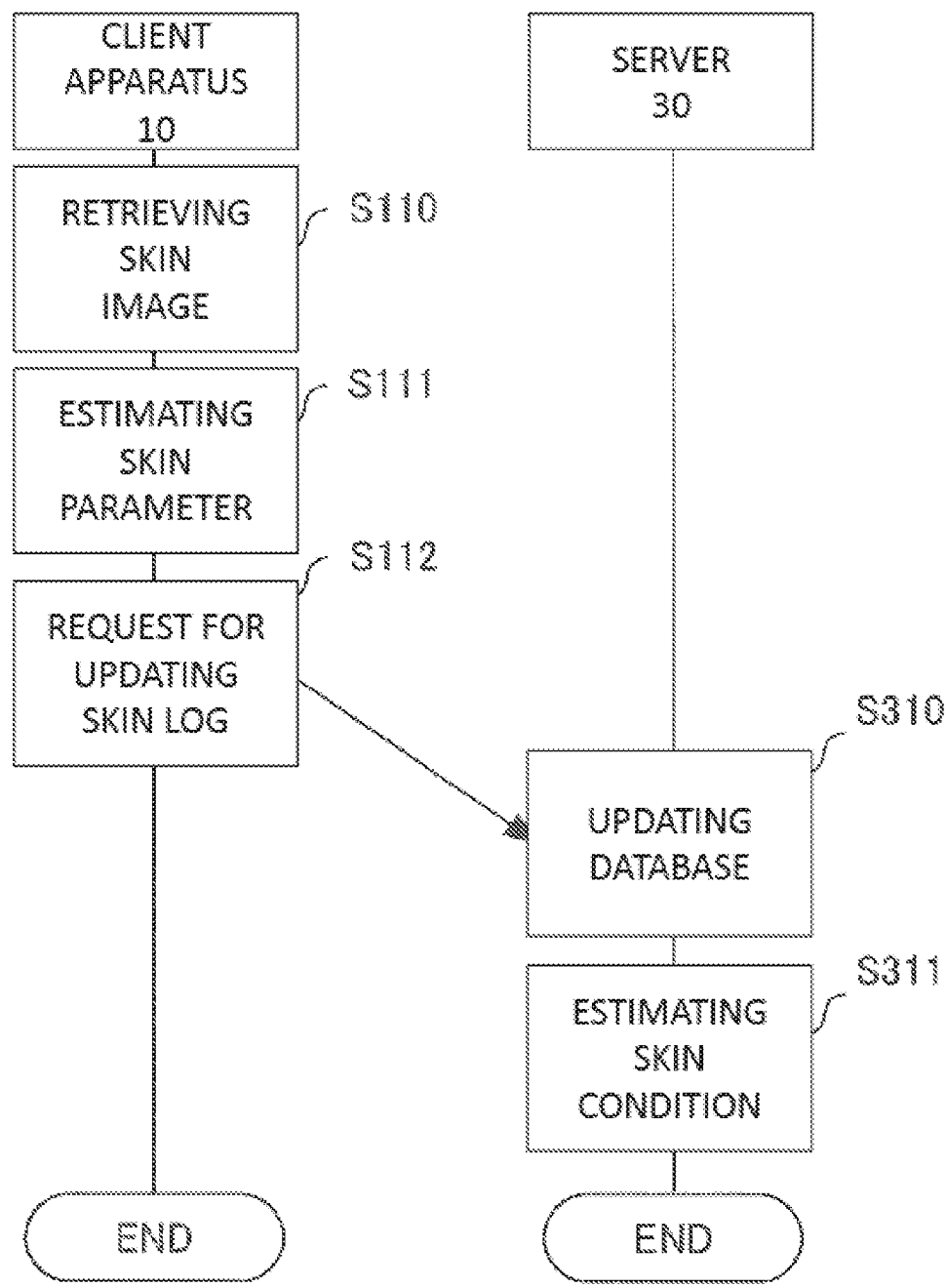
FIG. 15 is a flowchart of process for updating user log of an embodiment.

FIG. 15 is a flowchart of process for updating user log according to the present embodiment.

Of the steps in FIG. 15, the step executed by the client apparatus 10 is executed as a function of the cosmetic dispense application.

As shown in FIG. 15, the client apparatus 10 executes retrieving skin image (S110).

Specifically, the camera 16 captures an image of the users skin.

The processor 12 stores the captured image in the memory 11.

After step S110, the client apparatus 10 executes estimating skin parameter (S1*l*).

The processor 12 analyzes the image stored in the memory 11 in step S110.

The processor 12 calculates a user's skin color value, a moisture content value, and a sebum amount value by applying a predetermined algorithm to the analysis result of the image.

After step S111, the client apparatus 10 executes a skin log update request (S112).

Specifically, the processor 12 transmits skin log update request data to the server 30.

The skin log update request data includes the following information:
  use ID;
  information indicating the execution date and time of step S112;
  image data of the image captured in step S110; and
  skin color value, sebum amount value, and moisture amount value calculated in step S111.

After step S112, the server 30 executes updating database (S310) based on the skin log update request dat.

Specifically, the processor 32 adds a new record to the skin log information database (FIG. 9) associated with the user ID included in the skin log update request data transmitted in step S112.

The following information is stored in each field of the new record:
  in the "skin log ID" field, a new skin log D is stored;
  in the "date and time" field, information indicating the execution date and time of step S112 included in the skin log update request data is stored;
  in the "skin image" field, image data included in the skin log update request data is stored;
  in the "skin color" field, the value of the skin color included in the skin log update request data is stored;
  in the "water content" field, the value of the water content included in the skin log update request data is stored; and
  in the "sebum amount" field, the value of the sebum amount included in the skin log update request data is stored.

Thereby, the skin log information is updated.

After step S310, the server 30 executes estimating skin condition (S311).

Specifically, the processor 32 refers to the user information database (FIG. 5) and specifies an estimation formula associated with the user ID included in the skin log update request data.

The processor 32 calculates the skin score based on the skin log information by applying the skin log information updated in step S310 to the specified estimation formula.

The processor 32 stores information indicating the calculated skin score in the "first skin score" field of the skin evaluation log information database (FIG. 10) associated with the user ID.

(4-3) Cosmetic Dispense Processing

Figure 16:
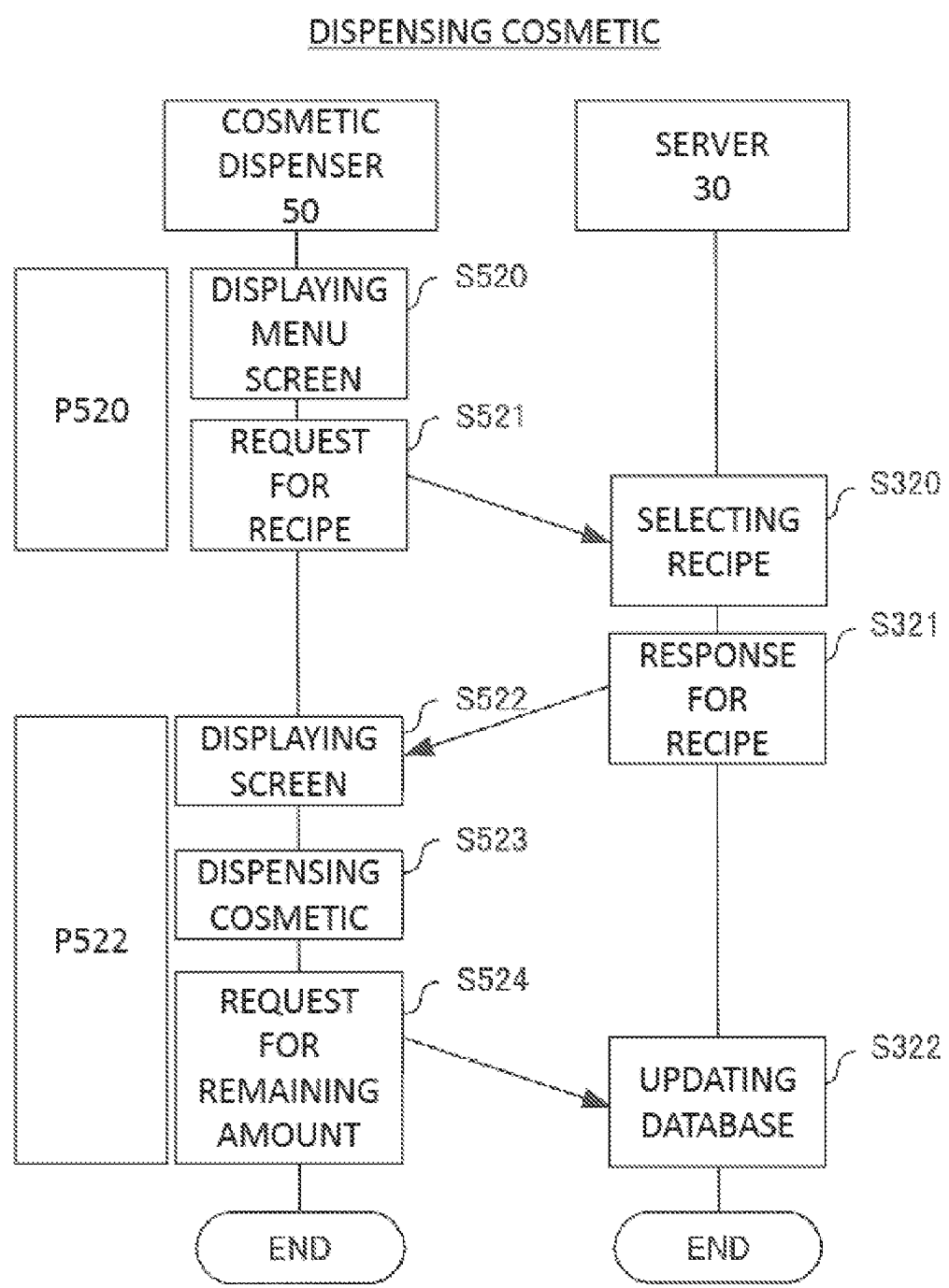
FIG. 16 is a flowchart of a process for dispensing cosmetics of an embodiment.
Figure 17:
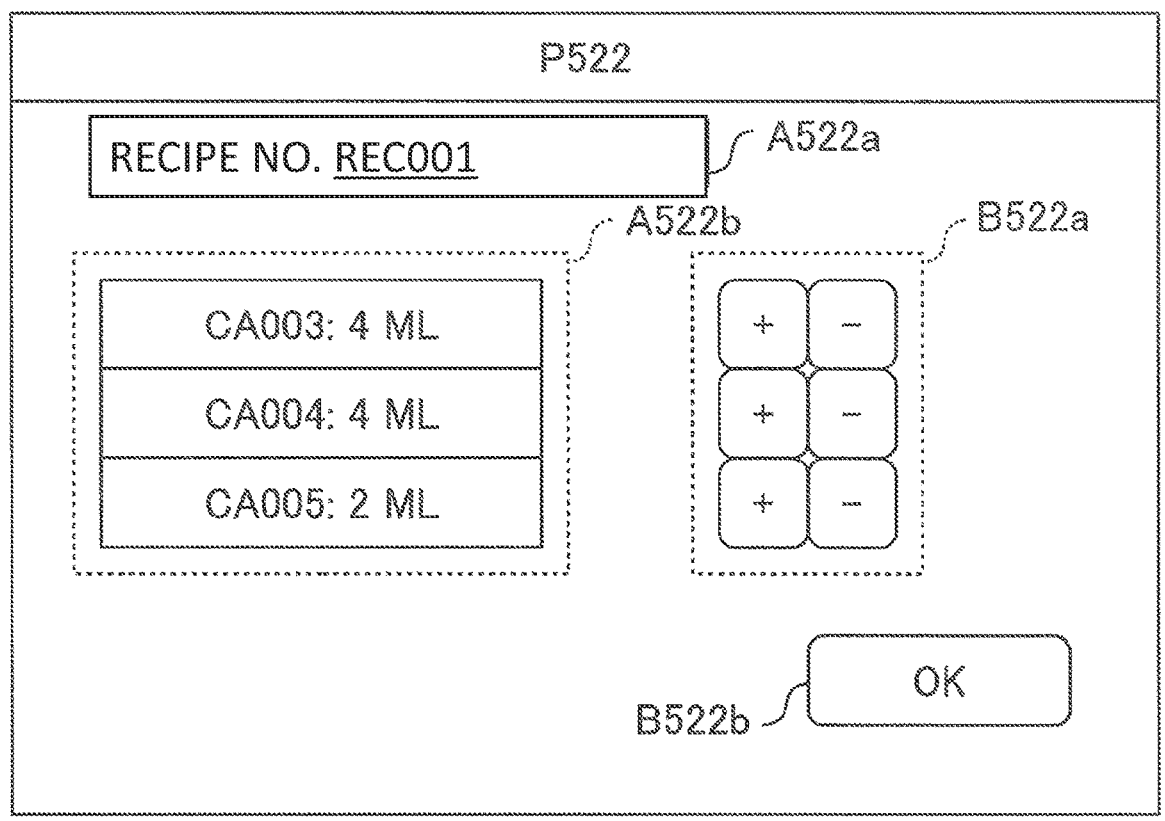
FIG. 17 is a diagram showing an example of a screen displayed in the information processing of FIG. 16.

FIG. 16 is a flowchart of the process of dispensing cosmetics according to the present embodiment. FIG. 17 is a diagram of a screen example displayed in the information processing of FIG. 16.

As shown in FIG. 16, the cosmetic dispenser 50 executes displaying menu screen (S520).

Specifically, the processor 52 displays a screen P520 on the display.

The screen P320 displays a button object B520.

The button object B520 is an object that receives a user instruction for dispense of cosmetics.

After step S520, cosmetic dispenser 50 executes a recipe request (S520).

Specifically, when the user operates the button object B520, the processor 52 transmits recipe request data to the server 30. The recipe request data includes the machine ID of the cosmetic dispenser 50.

After step S521, the server 30 executes selecting recipe (S320) based on the recipe request data.

Specifically, the processor 32 refers to the machine information database (FIG. 11) and specifies the owner user ID associated with the machine ID included in the recipe request data. The processor 32 refers to the skin evaluation log information database (FIG. 10) associated with the specified owner user ID, and specifies the latest skin score (for example, the first skin score of the record including the information indicating the latest date and time stored in the "date and time" field).

The processor 32 refers to the recipe information database (FIG. 12) and specifies a record in which the specified skin score is included in the range indicated by the information in the "condition" field.

The processor 32 specifies the recipe ID and the usage amount of each cosmetic base of the specified record.

After step S320, the server 30 executes a recipe response (S321).

Specifically, the processor 32 transmits recipe response data to the cosmetic dispenser 50.

The recipe response data includes the following information:
  recipe ID specified in step S320; and
  usage amount of each cosmetic base specified in step S320

After step S321, the cosmetic dispenser 50 executes displaying screen (S522) based on the recipe response data.

Specifically, the processor 52 displays the screen P522 on the display.

The screen P522 includes display objects A522*a* to A522*b* and button objects B522*a* to B522*b*.

In the display object A522*a*, the recipe ID included in the recipe response data is displayed.

In the display object A522b, the usage amount of each cosmetic base included in the recipe response data is displayed.

The button object B522a is an object that receives a user instruction to increase or decrease the usage amount of each cosmetic base shown in the display object A522b. The button object B522b is an object that receives a user instruction to determine the usage amount of each cosmetic be shown in the display object A522b.

After step S522, the cosmetic dispenser 50 executes dispensing cosmetic bases (S523).

Specifically, when the user operates the button object B522b, the processor 52 controls each of cartridges CA1 to CA5 so that each cosmetic base contained in each of the cartridges CA1 to CA5 is dispensed by the amount used for each cosmetic base shown in the display object A522b.

The cosmetic base contained in each of the cartridges CA1 to CA5 is dispensed from the dispense port 50ba. The user receives the dispensed cosmetic base by inserting the user's hand into the dispense port 50ba.

The received cosmetic bases are mixed as needed, and the customized cosmetics suitable for the user-unique factors may thereby be provided to the user.

After step S524, cosmetic dispenser 30 executes a remaining amount update request (S524).

Specifically, the processor 52 transmits remaining amount update request data to the server 30.

The remaining amount update request data includes the following information:
machine 1D, and
value indicating the dispense amount of the cosmetic base dispensed in step S523

After step S524, the server 30 executes updating database (S322).

Specifically, the processor 32 refers to the machine information database (FIG. 11) and specifies a record including the machine ID included in the remaining amount update request data.

The processor 32 subtracts the value of the dispense amount included in the remaining amount update request data from the value of the "cartridge" field of the specified record.

As a result, the remaining amount of the cosmetic base contained in each of the cartridges CA1 to CA5 is stored in the server 30.

According to the above embodiment, it is possible to provide a customized cosmetic suitable for the user-unique factors. However, the above represents n example of the information processing system preferably used in the present invention, and various variations are possible Several variations will be raised in the following, but the present invention is not limited to those.

(5) Variation
(5-1) First Variation

A first variation is an example in which a recipe is selected in consideration of a use's emotion when receiving cosmetics.

(5-1-1)Recipe Information Database

FIG. 18 is a diagram illustrating a data structure of a recipe information database according to the first variation.

As shown in FIG. 18, the recipe information database of the first variation includes an "emotion condition" field in addition to the fields of FIG. 12.

The "emotion condition" field stores an emotion code that is a reference in selecting recipe information. The emotion code is information indicating the user's emotion.

(5-1-2)Processing for Dispensing Cosmetics

Figure 19:
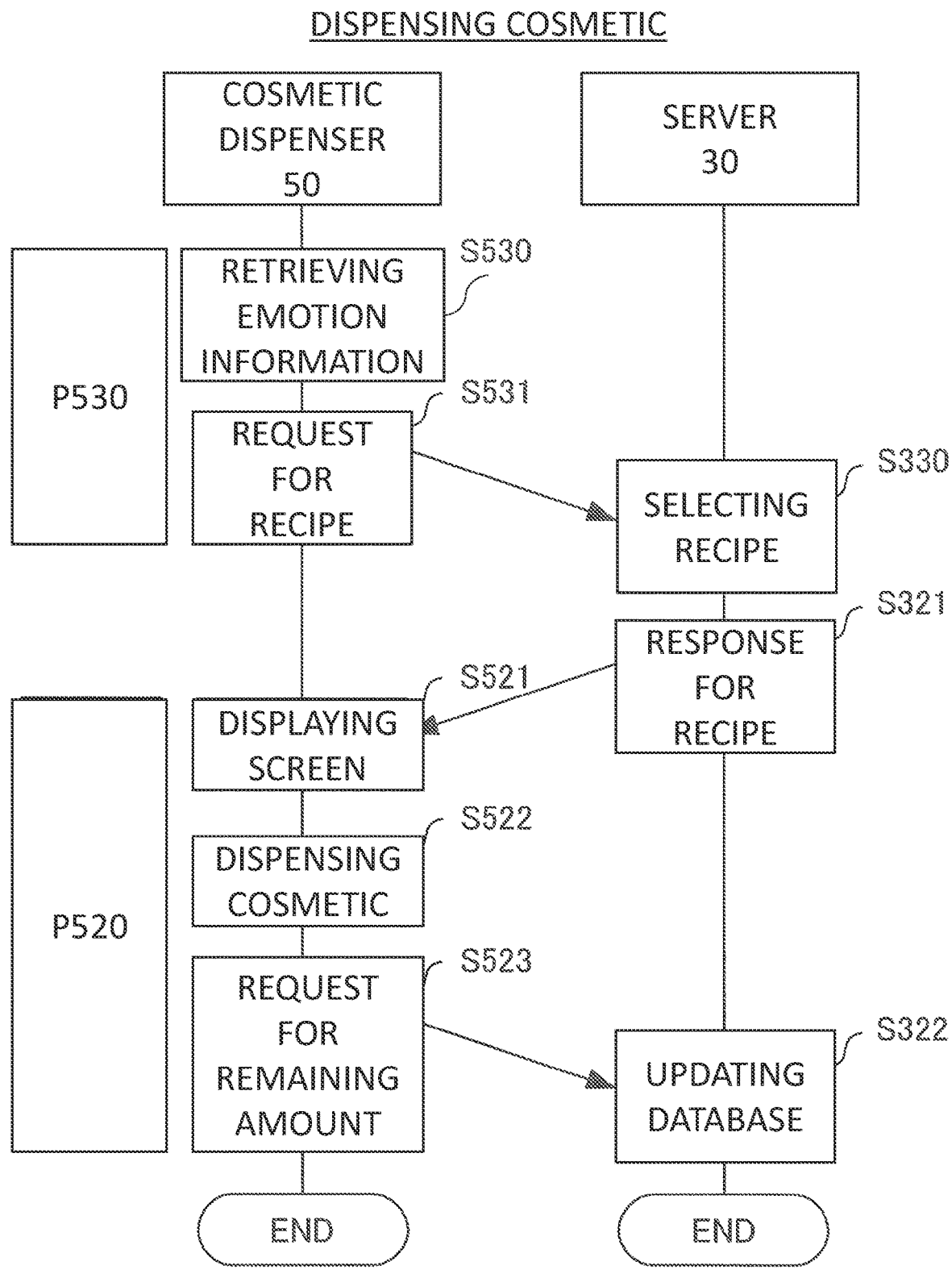
FIG. 19 is a flowchart of a process for dispensing cosmetics according to a first variation.

FIG. 19 is a flowchart of a process for dispensing cosmetics according to the first variation. FIG. 20 is a diagram of a screen example displayed in the information processing of FIG. 19.

As shown in FIG. 19, the cosmetic dispenser 50 executes retrieving emotion information (S530).

Specifically, when the user operates the button object B520, the processor 52 displays the screen P530 on the display.

The screen P530 includes button objects B530a to B530b. The button objects B530a to B530b are objects that receive designation of user emotions. Codes indicating emotions are assigned to the button objects B530a to B530b. When the user operates the button object B530a, the processor 52 receives an emotion code assigned to the button object B530a.

After step S530, the cosmetic dispenser 50 executes a recipe request (S531).

Specifically, the processor 52 transmits recipe request data to the server 30.

The recipe request data includes the following information:
machine ID of the cosmetic dispenser 50; and
emotion code received in step S530

After step S531, the server 30 executes selecting recipe (S330).

Specifically, the processor 32 refers to the machine information database (FIG. 11) and specifies the owner user ID associated with the machine ID included in the recipe request data.

The processor 32 refers to the skin evaluation log information database (FIG. 10) associated with the specified owner user ID, and specifies the latest skin score (for example, the first skin score of the record including the information indicating the first date of the latest date and time stored in the "date and time" field).

The processor 32 refers to the recipe information database (FIG. 12) and specifies a record in which the specified skin score is included in the information in the "condition" field. The processor 32 specifies a record in which the emotion code included in the recipe request data matches the information stored in the "emotion condition" field among the specified records.

The processor 32 specifies the recipe ID and the usage amount of each cosmetic base in the specified record (that is, the record based on the skin score and the emotion code).

After step S330, steps S321, S522 to S524, and S322 are executed in the same manner as in FIG. 16.

According to the first variation, a recipe based on the user's emotion is selected. As a result, it is possible to provide a cosmetic that is more suitable for user-unique factors at the very time.

(5-2) Second Variation

Figure 21:
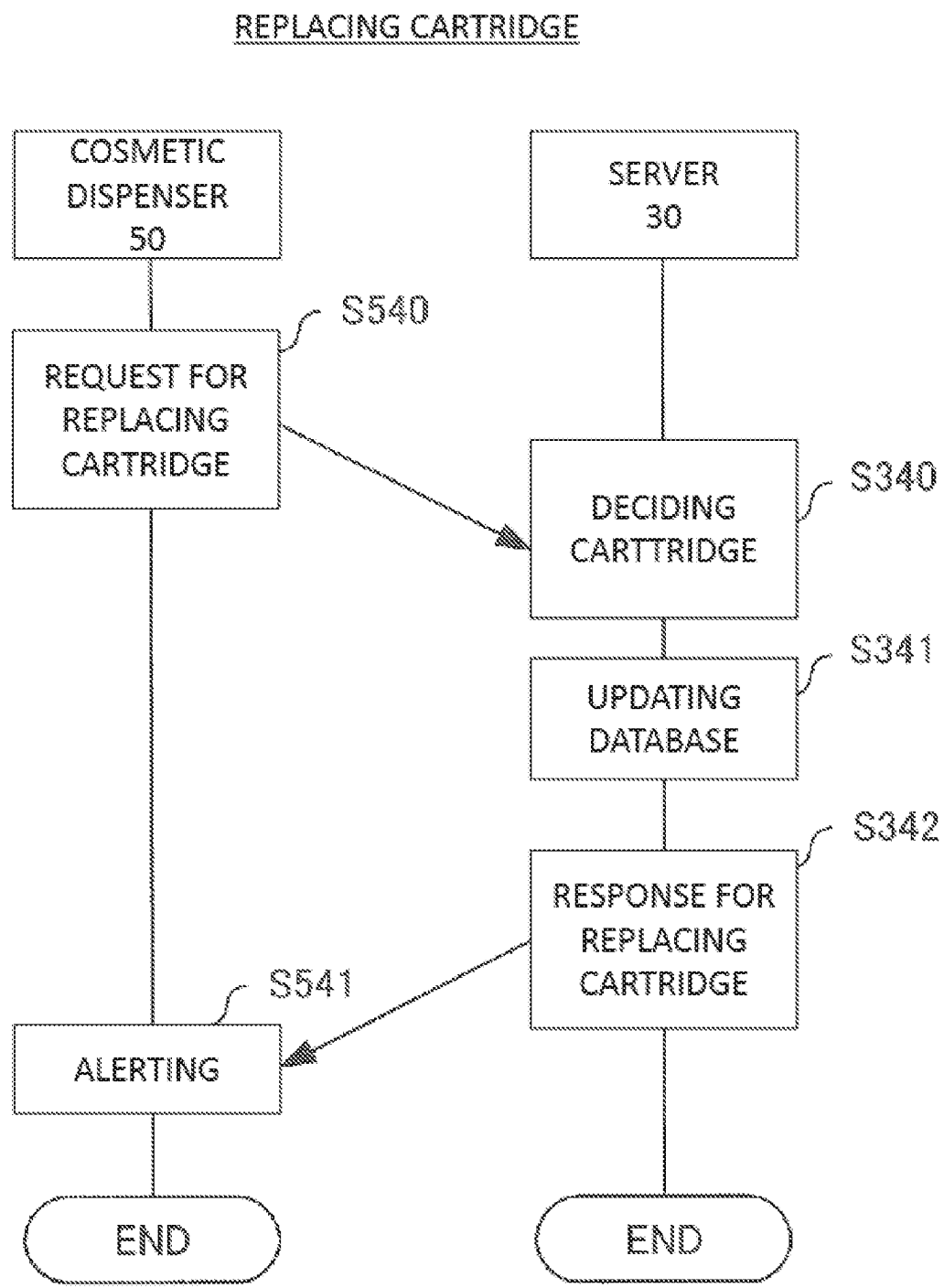
FIG. 21 is a flowchart of cartridge replacement processing according to a second variation.

A second variation is an example of information processing when the cartridges CA1 to CA5 are replaced. FIG. 21 is a flowchart of the cartridge replacement process of the second variation.

As shown in FIG. 21, the cosmetic dispenser 50 executes a cartridge replacement request (S540).

Specifically, after the user opens the upper part 50s and replaces the cartridge CA in the cartridge slots 50aa to 50se and then closes the upper part 50s, the processor 52 transmits cartridge replacement request data to the server 30.

The cartridge replacement request data includes the following information:
- machine ID of cosmetic dispenser 50;
- cartridge ID stored in IC chip CAa of the newly attached cartridge CA;
- remaining amount value stored in IC chip CAa of the newly attached cartridge CA; and
- information indicating the type of a cosmetic base stored in the IC chip CAa of the newly attached cartridge CA.

In the case that the newly attached cartridge CA is a non-genuine product, the cartridge replacement request data my not include at least one of the cartridge ID, the remaining amount value, and the type of the cosmetic base.

After step S540, the server 30 executes determining cartridge (S340).

Specifically, when the cartridge ID included in the cartridge replacement request data is not the predetermined cartridge ID, or when the cartridge replacement request data does not include the cartridge ID, the processor 32 determines that the newly attached cartridge CA is a non-genuine product.

After step S340, the server 30 executes updating database (S341).

Specifically, the processor 32 refers to the machine information database (FIG. 11) and specifies a record including the machine ID included in the cartridge replacement request data.

The processor 32 stores the cartridge ID and the remaining amount value included in the cartridge replacement request data in the "cartridge" field of the specified record.

In the case that the processor 32 determines in step S340 that the product is a non-genuine product, the processor 32 may store a code indicating the non-genuine product in the "cartridge" field.

After step S341, the server 30 executes a cartridge replacement response (S342).

Specifically, the processor 32 transmits cartridge replacement response data to the cosmetic dispenser 50. If it is determined as non-genuine product in step S340, the cartridge replacement response data includes a message indicating that the newly attached cartridge CA is a nongenuine product.

After step S342, the cosmetic dispenser 50 executes alerting (S541).

Specifically, the processor 52 displays a message included in the cartridge replacement response data on the display.

According to the second variation, the server 30 may store the information indicating that the newly attached cartridge CA is a non-genuine product and alert this information to the (5-3) Third Variation A third variation is an example of the configuration of the cosmetic dispenser 50.

(5-3-1) Configuration of Cosmetic Dispenser

Figure 22:
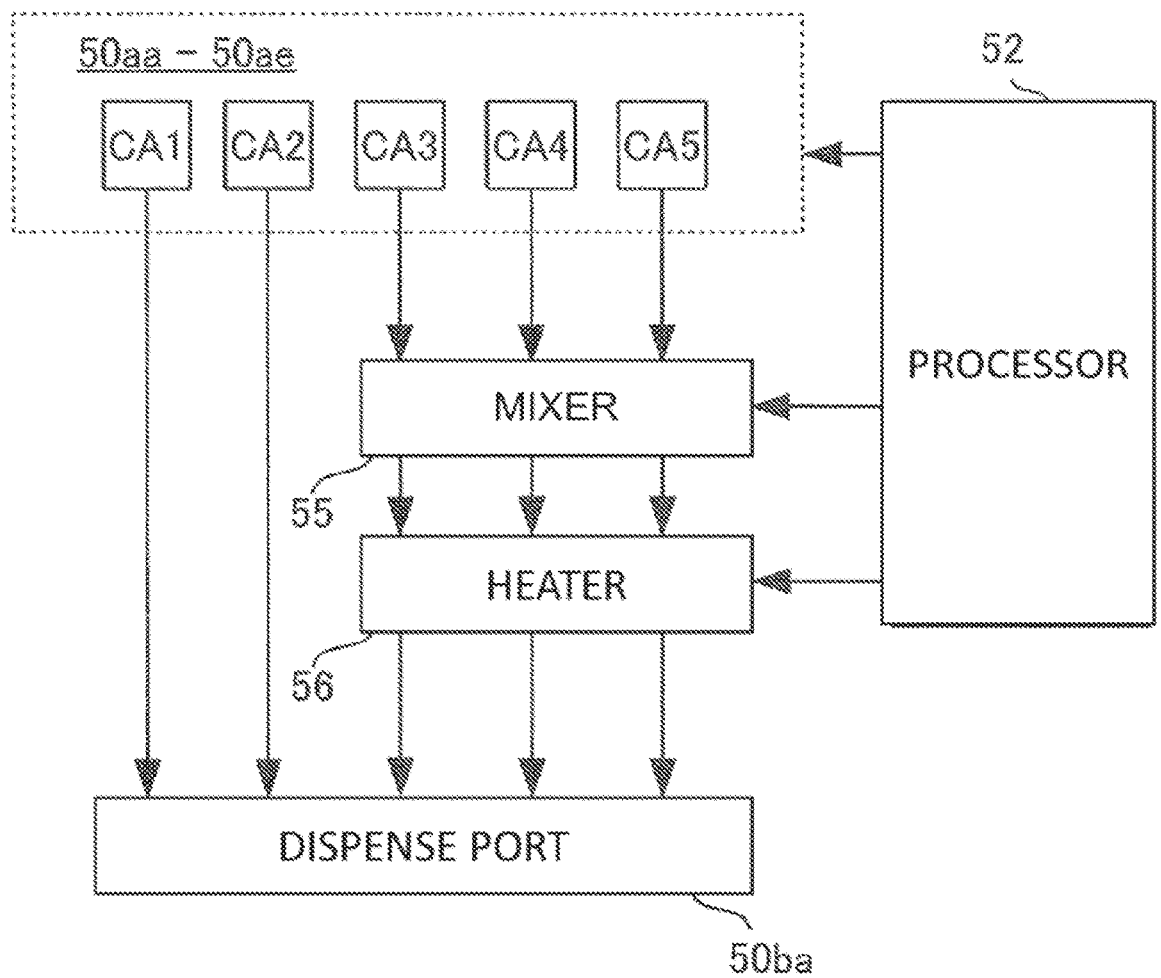
FIG. 22 is a schematic diagram showing a configuration of a cosmetic dispenser according to a third variation.

The configuration of the cosmetic dispenser of the third variation will be described. FIG. 22 is a schematic diagram illustrating a configuration of a cosmetic dispenser according to a third variation.

As shown in FIG. 22, the cosmetic dispenser 30 includes a mixer 55 and a heater 56 in addition to the configuration of FIG. 3.

The mixer 55 is configured to mix cosmetic bases contained in the cartridges CA3 to CA5. For example, the mixer 33 may be a hollow container including a stirrer.

The processor 32 controls the mixer 33 to mix and dispense the cosmetic bases contained in the cartridges CA3 to CA5.

The cosmetic bae to be mixed we not limited to the cosmetic bases contained in the cartridges CA3 to CA5, but two or more arbitrary cosmetic base contained in the cartridges CA1 to CA5 may be mixed.

The heater 56 is configured to heat the cosmetic bases contained in the cartridges CA3 to CA5. For example, the heater 56 may be a hollow container including a heating module such a an electric heater.

The processor 52 controls the heater 56 to heat and dispense the cosmetic bases contained in the cartridges CA3 to CA5.

The cosmetic bases to be heated are not limited to the cosmetic bases contained in the cartridges CA3 to CA5, but two or more arbitrary cosmetic base contained in the cartridges CA1 to CA5 may be heated.

(5-3-2) Recipe Information Database

FIG. 23 is a diagram illustrating a data structure of a recipe information database according to the third variation.

As shown in FIG. 23, the recipe information database of the third variation includes a "mixer" field and a "heater" field in addition to the fields shown in FIG. 12.

The "mixer" field includes a "mixing speed" field, a "mixing order" field, and a "mixing time" field.

The "mixing speed" field stores a value indicating the mixing speed by the mixer 55. The "mixing order" field stores cartridge slot IDs indicating the mixing order by the mixer 55. The cartridge slot ID is information for identifying the cartridge slots 50ac to 50ae.

The "mixing time" field stores a value indicating the mixing time by the mixer 55.

The "heater" field includes a "heating temperature" field and a "heating time" field.

The "heating temperature" field stores a value indicating the heating temperature of the heater 56.

The "heating time" field stores a value indicating the heating time of the heater 56.

(5-3-3) Dispensing Cosmetics

A process of dispensing cosmetics according to the third variation will be described.

In step S320 of FIG. 16, the processor 32 specifies a record whose skin score is included in the range indicated by the information in the "condition" field, and then specifies the recipe ID, the usage amount of each cosmetic base, and the control information (heating temperature and heating time), of the specified record.

In step S321, the processor 32 transmits recipe response data to the cosmetic dispenser 50.

The recipe response data includes the following information:
- recipe ID specified in step S320;
- usage amount of each cosmetic base specified in step S320;
- control information of the mixer 33 specified in step S320; and
- control information of the heater 56 specified in step S320.

In step S523, the processor 52 controls the cartridges CA3 to CA5, the mixer 3, md the heater 56 based on the usage amount and the control information included in the recipe response data.

According to the third variation, the user may receive the cosmetic bases nixed and heated based on the user-unique information.

(5-4) Fourth Variation

A fourth variation is mi example in which an emulsion base and a cosmetic liquid base are contained in the cartridge CA.

The different types of emulsion bases may be contained in the cartridges CA1 to CA2 of the fourth variation, and different types of cosmetic liquid bases may be contained in the cartridges CA3 to CA5.

For example, the emulsion base contained in the cartridge CA1 is dispensed when the process of dispensing cosmetics is executed in the time zone after waking up (for cap, 6:00 to 8:00). That is, the emulsion base contained in the cartridge CA1 is an emulsion for morning use. The emulsion for morning use contains ingredients suitable for utilization prior to a day's activity.

The emulsion base contained in the cartridge CA2 is dispensed when the process of dispensing cosmetics is executed in a time zone before going to bed (for example, 22:00 to 24:00). That is, the emulsion base contained in the cartridge CA2 is an emulsion for night use. The emulsion for night use contains ingredients suitable for utilization before going to bed.

The cosmetic liquid base contained in the cartridges CA3 to CA5 is dispensed based on the recipe information.

(5-5) Fifth Variation

A fifth variation is an example in which the preparation used for the makeup is contained in the cartridge CA.

As a first example, the cartridge CA1 contains a base that gives a weakly glossy texture (so-called matte texture).

The cartridge CA2 contains a base that gives a glossy texture.

The cartridge CA3 contains a moisturizer base. The moisturizer base includes, for example, ma ingredient that moisturizes the skin, an ingredient that prevents ultraviolet rays, or a combination thereof.

The cartridge CA4 contains a foundation base having a color tone (hue and saturation in the Munsell color system) that matches the user's skin color and high brightness.

The cartridge CA5 contains a foundation base having a color tone (hue and saturation in the Munsell color system) that matches the users skin color and low brightness.

In step S320, the processor 32 specifies the owner user ID, refers to the skin log information database (FIG. 9) associated with the specified owner user ID, and specifies the latest skin color (for example, the skin color of the record in which the information of "data and time" field is the latest).

In the case that the specified skin color is lighter than a predetermined threshold, the processor 32 selects a recipe having a high blending ratio of the base contained in the cartridge CA4. In the case that the specified skin color is darker than a predetermined threshold value, the processor 32 selects a recipe having a high blending ratio of the base contained in the cartridge CA5.

The second example differs from the first example in the following points:
the cartridge CM contains a foundation base that has a color tone that matches the user's skin color (hues, saturation, and brightness in the Munsell color system) and that has a high cover level, and
the cartridge CA5 contains a foundation base that has a tone that matches the user's skin color (hues, saturation, and brightness in the Munsell color system) and that has a low cover level.

The cover level is the magnitude of the effect of hiding skin spots and freckles.

In step S320, after specifying the owner user ID, the processor 32 refers to the skin log information database (FIG. 9) associated with the specified owner user ID and specifies the latest moisture content (for example, the moisture content of the record whose the information of the "date and time" field indicates the latest date and time).

When the specified amount of water is higher than a predetermined threshold, the processor 32 selects a recipe having a high blending ratio of the base contained in the cartridge CA4. Alternatively, the processor 32 selects a recipe having a low blending ratio of the moisturizer base contained in the cartridge CA3.

When the specified amount of water is equal to or less than de predetermined threshold, the processor 32 selects a recipe having a high blending ratio of the base contained in the cartridge CA5. Alternatively, the processor 32 selects a recipe having a high blending ratio of de moisturizer base contained in the cartridge CA3.

(5-6) Sixth Variation

Figure 24:
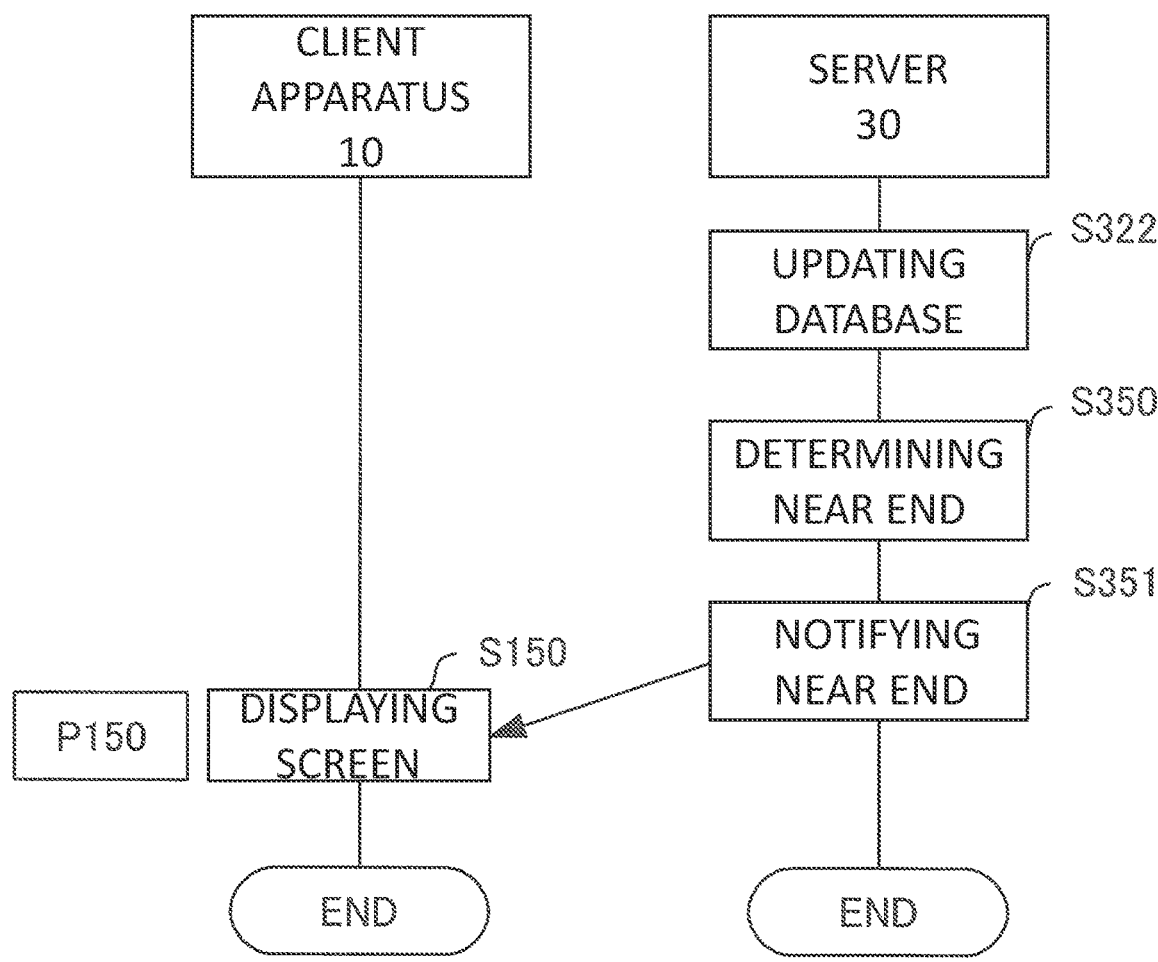
FIG. 24 is a flowchart of a near-end notification process according to a sixth variation.

A sixth variation is an example in which a predetermined notification is given to the user when the remaining amount of cosmetic bases contained in the cartridge CA has been little. FIG. 24 is a flowchart of the near-end notification process according to the sixth variation.

Figure 25:
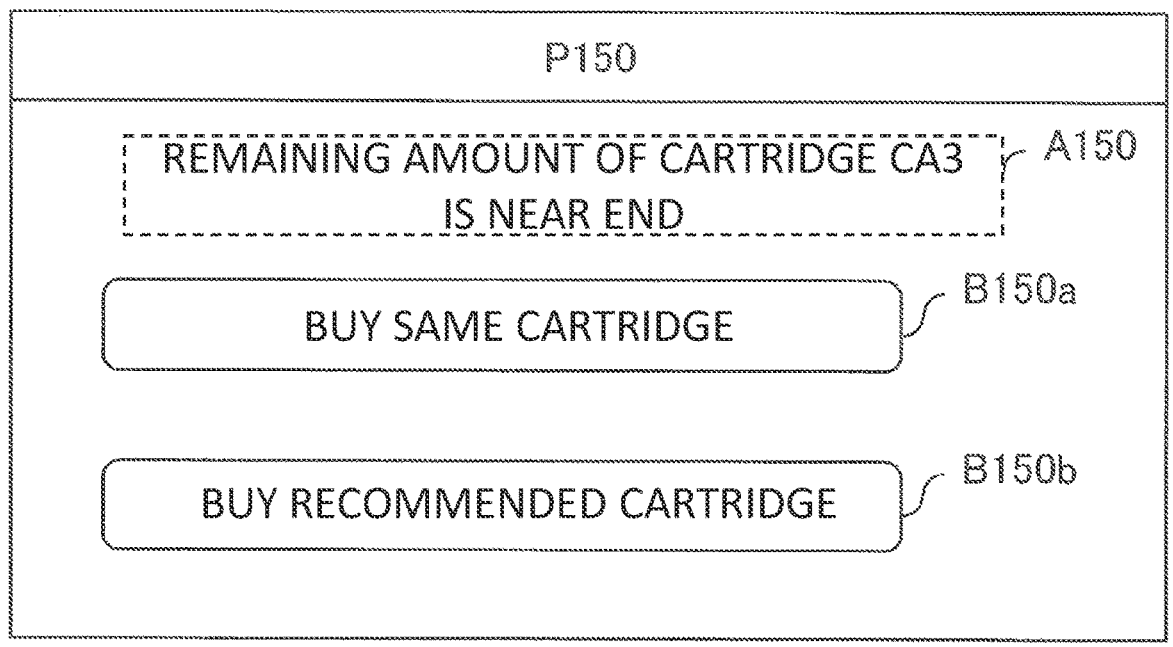
FIG. 25 is a diagram showing an example of a screen displayed in the information process of FIG. 24.

FIG. 25 is a diagram of a screen example displayed in the information processing of FIG. 24.

As shown in FIG. 24, the server 30 executes determining near-end (S350) after step S322(FIG. 16).

Specifically, the processor 32 refers to the machine information database (FIG. 11) updated in step S322, and specifies the cartridge (hereinafter referred to as "nearend cartridge") whose remaining amount value of cosmetic bases is equal to or less than a predetermined threshold among the "cartridge" field.

The server 30 executes notifying new-end (S351).

Specifically, the processor 32 transmits near-end notification data to the client apparatus 10 in which the cosmetic dispense application associated with the owner user ID specified in step S320 is installed.

The client apparatus 10 executes displaying screen (S150) based on the near-end notification data.

Specifically, the processor 12 displays the screen P150 on the display.

The screen P150 includes display object A150 and button objects B150a to B150b. The display object A150 indicates a message indicating the cartridge specified a the near-end cartridge in step S350.

A URL (Uniform Resource Locator) of a purchase site for purchasing a cartridge of the same type as the cartridge specified as the new-end cartridge is assigned to the button object B150a. When the user operates the button object B150a the processor 12 accesses the URL assigned to the button object B150s.

A URL of a purchase site for purchasing a cartridge recommended for the user is assigned to the button object B150b. When the user operates the button object B150b, the processor 12 accesses the URL assigned to the button object B150b.

In the sixth variation, the server 30 may execute the purchase and delivery processing for the cartridge specified a the now-end cartridge, instead of the notifying near-end (S351).

In this case, the user my receive a new cartridge without any operation.

According to the sixth variation, the user may utilization the cosmetic dispenser 50 without paying mind to the remaining amount of the cartridge.

(5-7) Seventh Variation

Figure 26:
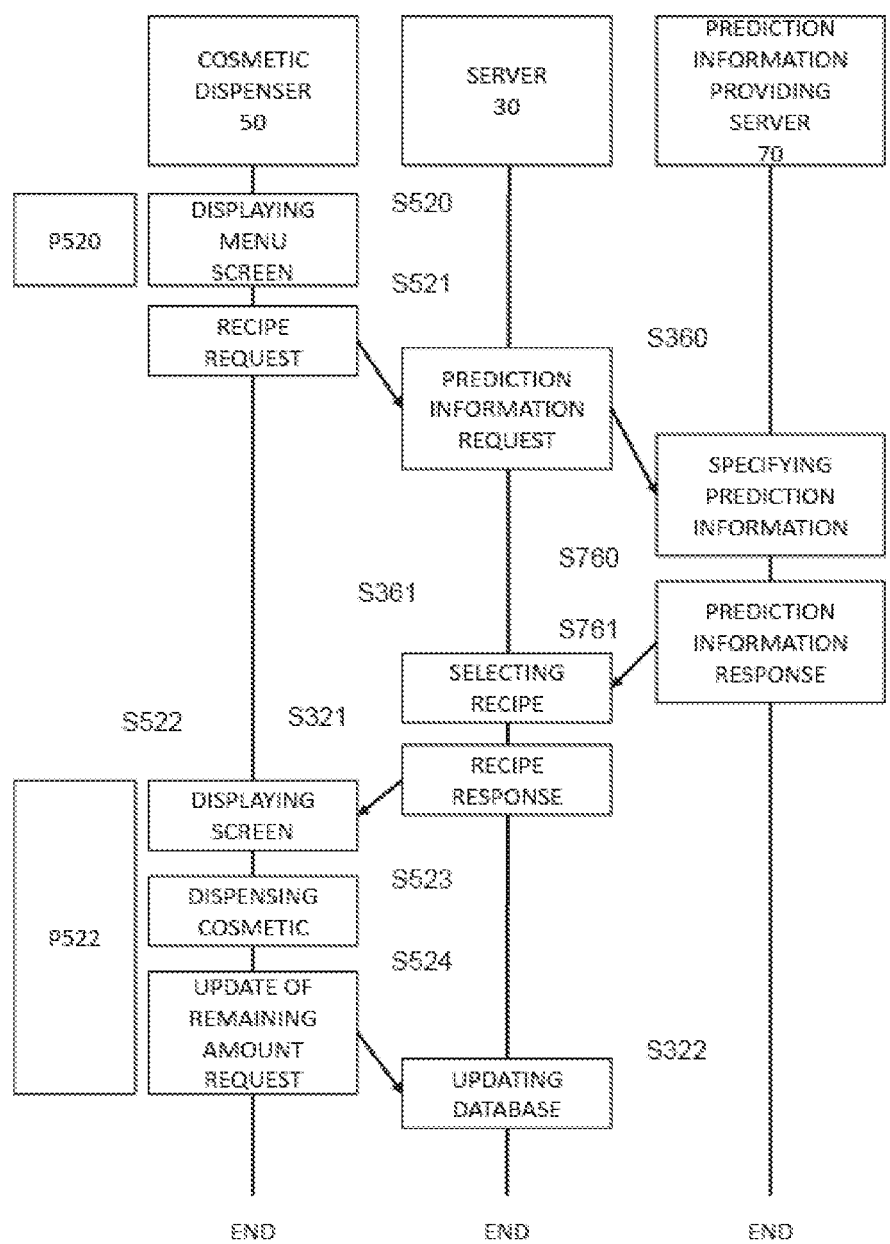
FIG. 26 is a flowchart of a process for dispensing cosmetics according to a seventh variation.

A seventh variation is an example in which a recipe is selected based on information stored in the prediction information providing server 70. FIG. 26 is a flowchart of a process for dispensing cosmetics according to the seventh variation.

As shown in FIG. 26, after step S521 (FIG. 16), the server 30 executes a prediction information request (S360).

Specifically, the processor 32 refers to the machine information database (FIG. 11) and specifies the owner user ID associated with the machine ID included in the recipe request data.

The prediction information providing server 70 stores a user ID, environment prediction information, action prediction information, and psychosomatic prediction information in association with each other.

The processor 32 transmits the prediction information request data to the prediction information providing server 70. The prediction information request data includes the specified owner user ID.

After step S360, the prediction information providing server 70 executes specifying prediction information (S760).

Specifically, the prediction information providing server 70 specifies prediction information (at least one of environmental prediction information, action prediction information, and psychosomatic prediction information) associated with the user ID included in the prediction information request data.

After step S760, the prediction information providing server 70 executes a prediction information response (S761).

Specifically, the prediction information providing server 70 transmits prediction information response data to the server 30. The prediction information response data includes the prediction information specified in step S760.

After step S761, the server 30 executes selecting recipe (S361).

As a first example, the processor 32 specifies the latest skin score and de corrects the skin score based on the prediction information included in the prediction information response data.

As an example, when de prediction information is environment prediction information indicating a rain forecast, the processor 32 corrects the skin score on the assumption that the user goes to a environment with high humidity.

As another example, when the prediction information is action prediction information indicating exercise, the processor 32 corrects the skin score an the assumption that the user exercises.

As another example, when the prediction information is psychosomatic prediction information related to the psychosomatic, the processor 32 corrects the skim score on the assumption that the amount of sebum secretion increases (that is, deterioration of the skin condition).

The processor 32 refers to the recipe information database (FIG. 12) and specifies a record in which the corrected skin score is included in the range indicated by the information in the "condition" field.

The processor 32 specifies the recipe ID and the usage amount of each cosmetic base of the specified record.

As a second example, the same base as that of the first example of the fifth variation is contained in the cartridges CA1 to CA5.

The "condition" field of the recipe information database (FIG. 12) stores the contents of the prediction information as a reference when selecting recipe information. The content of the prediction information indicates an event that does not affect the skin condition.

The processor 32 refers to the recipe information database (FIG. 12) and specifies a record whose information in the "condition" field matches the prediction information.

The processor 32 specifies the recipe ID of the specified record and the usage amount of each cosmetic base.

As an example, when the action prediction information indicates an action in which a glossy make is preferred (for example participation in a party), the processor 32 selects the recipe indicating the blending ratio of the base contained in the cartridge CA2 higher than that in the cartridge CA1.

As another example, when the action prediction information indicates an action (participation in a business meeting) in which conservative make is preferred, the processor 32 selects the recipe indicating the mixing ratio of the base contained in the cartridge CA1 higher than that in the cartridge CA2.

According to the seventh variation, the user may be provided with a customized cosmetic product suitable to both the user log information (that is, factors unique to the past user) and the prediction information (that is, factors specific to the future user).

(5-8) Eighth Variation

An eighth variation is an example in which a recipe is selected in consideration of prediction information.

In step S320 (FIG. 16), after specifying the owner user ID, the processor 32 specifies either the first skin score or the second skin score according to the execution time of the process. For example, when the execution time is from 6:00 to 8:00, the processor 32 specifies the latest first skin score. When the execution time is from 22:00 to 24:00, the processor 32 specifies the latest second skin score.

The processor 32 refers to the recipe information database (FIG. 12) and specifies a record in which the specified skin score (first skin score or second skin score) is included in the range indicated by the information in the "condition" field.

The processor 32 specifies the recipe ID and the usage amount of each cosmetic base of the specified record.

According to the eighth variation, the skin score to be referenced for selecting a recipe is switched according to the time when the user uses the cosmetic dispenser 50. In particularly, after waking up, a recipe is selected with reference to the first skin score based on past user-unique information. Before going to (the) bed, a recipe is selected with reference to the second skin score based on past user-unique information and future user-unique information.

Thereby, the customized cosmetics suitable for a users lifestyle may be provided.

(5-9) Ninth Variation

A ninth variation is an example in which the amount of cosmetics dispensed by the cosmetic dispenser 50 is adjusted for each user.

The user information database (FIG. 5) further stores size information indicating the size of a part (for example, a face) to which cosmetics are to be applied. The size information may be determined based on a user instruction or may be estimated from the image of the part.

In step S321 (FIG. 16), the server 30 specifies size information associated with the owner user ID specified in step S320.

The server 30 transmits recipe response data to the cosmetic dispenser 50.

The recipe response data includes the following information:
the recipe ID specified in step S320;
the usage amount of each cosmetic base specified step S320; and
the specified size information.

In step S523, the cosmetic dispenser 50 determines the usage amount of the cosmetic base to be dispensed on the basis of the size information included in the recipe response data.

Specifically, the processor 52 determines the usage amount of the cosmetic base based on the size information.

The processor 52 controls the cartridges CA1 to CA5 so that the cosmetic bases contained in the cartridges CA1 to CA5 are dispensed by the determined usage amount.

The usage amount of cosmetic bases may be the dispense amount of each of the cartridges CA1 to CA5 or the total amount of cosmetic bases dispensed from the cartridges CA1 to CA5.

According to the ninth variation, it may provide an amount of customized cosmetics suitable for the user.

(6) Summary of Above Embodiment

The first aspect of the above embodiment is an information processing apparatus (for example, a server 30) capable of commutating with a cosmetic dispenser 50 configured to dispense at least one of a plurality of cosmetic bases based on recipe information (FIG. 12) indicating a usage amount of each of the plurality of cosmetic bases, the apparatus comprising:

- a retrieve module (for example, the processor 32 executing step S320) configured to acquire user-unique information unique to the user, the user-unique information including at least one of user attribute information related to the uses attributes, environmental information related to the use's environment, action information related to the use's action, and psychosomatic information related to the use's psychosomatic, skin information related to the uses skin, md information related to cosmetics which the user has used
- a selection module (for example, the processor 32 executing step S320) configured to select the recipe information based on the user-unique information among a plurality of recipe information; and
- a transmission module (for example, the processor 32 executing step S321) configured to transmit the selected recipe information to the cosmetic dispenser 50.

According to this first aspect, it is possible to provide a customized cosmetic suitable for a user-unique factor.

In particular, it is possible to provide a customized cosmetic suitable for at least one of the user's attributes, the user's environment, the user's action, the user's psychosomatic, the user's skin, and cosmetics which the user has used In the second aspect of the above embodiment, the user attribute information includes information indicating at least one of age, gender, and address of the user.

In the third aspect of the above embodiment, the environmental information includes information indicating at least one of the temperature, humidity, and UV exposure amount of the environment spent by the user.

In the fourth aspect of the above embodiment, the action information includes information indicating at least one of a meal, an exercise, sleep, an energy consumption, and a location of the user.

In the fifth aspect of the above embodiment, the psychosomatic information includes a pulse value, a sexual cycle, stress index, and mindfulness index, height, weight, body fat, a skin humidity retention level, a skin wrinkle level, and a skin spot level of the user.

In the sixth aspect of the above embodiment, the recipe information includes information indicating a usage amount or a blending ratio of the cosmetic bases contained in each cartridge.

In the seventh aspect of the above embodiment, the user-unique information includes user log information (FIGS. 6 to 10)indicating the history of the user-unique information.

In the eighth aspect of the above embodiment, further comprising a module (for example, the processor 32 executing step S341) configured to store cartridge information related to a cartridge CA containing the cosmetic bases associated with machine ID that identifies the cosmetic dispenser 50.

According to the eighth aspect of the above embodiment, the server 30 may manage information (FIG. 11) on the cartridge CA set in the cosmetic dispenser 50.

In the ninth aspect of the above embodiment, the cartridge information includes information (FIG. 11) indicating a remaining amount of cosmetic bases contained in the cartridge.

According to the ninth aspect of the above embodiment, the server 30 may minge the remaining amount of cosmetic bases contained in the cartridge CA set in the cosmetic dispenser 50.

A tenth aspect of the above embodiment is a cosmetic dispenser 50 capable of communicating with the information processing apparatus (for example, server 30), the cosmetic dispenser 50 including:

- a plurality of cartridge slots 50aa to 50ae, each cartridge slot 50aa to 50ae configured to hold a cartridge CA containing a cosmetic base, each cartridge detachable with each cartridge slot; end
- a dispenser (for example, the processor 52 executing step S522) configured to dispense the cosmetic base contained in each cartridge CA held by each of the plurality of cartridge slot 50aa to 50ae based on the recipe information transmitted from the information processing apparatus (for example, server 30) and dispense the customized cosmetic based on the recipe information.

In the eleventh aspect of the above embodiment, the dispenser dispenses the cosmetic bases contained in each cartridge CA based on the recipe information.

In the twelfth aspect of the above embodiment, the dispenser mixes the cosmetic bases contained in the cartridges and dispenses the mixed cosmetics based on the recipe information.

In the thirteenth aspect of the above embodiment, further comprising a transmission module (for example, the processor 52 executing step S523) configured to transmit cartridge information relating to the cartridge CA held in the cartridge slots 50aa to 50ae to the information processing apparatus (for example, the server 30).

In the fourteenth aspect of the above embodiment, the cartridge information includes information indicating the remaining amount of cosmetic bases contained in the cartridge CA.

(7) Other Variations

The memory 11 may be connected to the client apparatus 10 via the network NW. The memory 31 may be connected to the server 30 via the network NW. The memory 51 may be connected to the cosmetic dispenser 50 via the network NW.

Each step of the above information processing may be executed by any one of the client apparatus 10, the server 30, and the cosmetic dispenser 50.

The recipe information database (FIG. 12) may include a "blending ratio" field instead of the "usage amount" field.

The "blending ratio" field stores information indicating the blending ratio of the cosmetic bases contained in the cartridges CA1 to CA5.

In step S523 (FIG. 16), the processor 52 dispenses the cosmetic bases contained in the cartridges CA1 to CA5 so that the total amount of the cosmetic bases to be dispensed becomes a constant amount at a rate based on the information indicating the blending ratio.

This example is particularly preferable when the base used for the makeup is contained in the cartridge CA as in the fifth variation.

The server 30 may acquire the user log information (at least one of environment log information, action log information, and psychosomatic log information) from an apparatus (for example, an external server) other than the wearable device 90. In this case, the external server stores a user ID and user log information in association with each other.

The psychosomatic log information may further include the following information:
use's height;
use's weight; and
users body fat.

The skin log information may further include the following information:
information indicating the skin humidity retention level;
information indicating the level of skin wrinkle; and
information indicating the level of skin spots.

The server 30 may further select a recipe based on at least one of the following:
user attribute information (FIG. 5);
used cosmetic ID (FIG. 5); and
inquiry (FIG. 5).

The skin log information database of FIG. 9 includes a "skin color" field, a "water content" field, and "sebum" field which store the measurement value measured by the measurement apparatus.

By using the information processing system or the like described in detail above, the cosmetics customized based on the user-unique information are dispensed to the user, for example, from the dispense port 30ba of the cosmetic dispenser shown in FIG. 2A. In the example of FIG. 2A, the user inserts the user's hand into the dispense port 50ba, ad the cosmetic base is dispensed onto the hand.

As a specific dispensing mode, there are modes in which the cosmetic bases contained in the respective cartridges are separately dispensed from a plurality of dispense ports (nozzles or the like) connected with the respective cartridges ad in which tubular members conveying cosmetic bases from the cartridges to the dispense port we caused to communicate with each other in the dispenser (for example, in the vicinity of the dispense port) and mixed cosmetic base are dispensed from a dispense port. Alternatively, a mode is possible in which the user picks predetermined amounts of predetermined cosmetic bases from the cartridges and mixes those him/herself according to the recipe information acquired from the information processing System.

In either of the modes, the user finally uses cosmetic bases or a base mixture by appropriately mixing the cosmetic bases or the base mixture on the hand. In this case if the mixability among cosmetic bases are low, this may affect the user's emotion. In other words, even if the cosmetic bases of the composition suitable for the user on the very day mad at the very time, the cosmetics may become unsuitable for the users emotion in use of the cosmetics due to the change in the stress index of the user in mixing the bases. Consequently, it is important to prepare the cosmetic bases configuring the customized cosmetics, in other words, the cosmetic bases contained in the above cartridges CA1 to CA5 such that those are properly mixed with each other.

The cosmetic kit according to the present invention includes a plurality of cosmetic bases, and the cosmetic bases are mixable with each other. Consequently, the user may mix the bases without feeling stress and use the customized cosmetics.

In the present invention, a new index representing the mixability of bases is set, and a base satisfying the condition based on the index is defined as mixable (easily homogenized).

Specifically, when the absorbance of the mixture in a container is measured while the container filled with at least two types of bases are rotated at a predetermined speed, the time in which the change ratio of the absorbance per unit time becomes ±5% or lower is used as a parameter, and whether the value of the parameter is within 35 minutes is used as an index of whether or not the bases are mixable (easily homogenized) with each other.

The index may be measured, for example, as follows.
A diffuse reflection measurement accessory (ACC101) is attached to a near-infrared ray measurement apparatus (MB3600) of ABB Ltd.

A screw tube (20 ml) is filled with 8 g in total of a base sample, the base sample is placed in a rotation apparatus accompanying the ACC101, and the absorption of near-infrared rays of the base sample in the screw tube is measured while the base sample is rotated at 3 RPM. The measurement is conducted under measurement conditions of; a wavenumber region of 4,000 to 10,000 K ($K=cm^{-1}$); resolution of 8 K; and the number of scans of 16 scans.

When an absorbance in 4,000 to 10.000 K obtained in a measurement is set as f(K), an integrated value (A) of absorbance for one measurement is represented by the following equation (1).

[Expression 1]

$$A\text{(Integrated value of absorbance)} = \int_{4000}^{10000} f(K) dK \quad (1)$$

The measurement is conducted at a frequency of one measurement per 30 seconds while the above rotation is continued. Given that the integrated value of absorbance (equation (1)) in the nth measurement is "An", a change ratio (Rn) of the integrated value of absorbance between the nth measurement and n+1th measurement is represented by the following equation.

[Expression 2]

$$Rn\text{(change ratio)} = \frac{A_{n+1}}{A_n} \times 100 \quad (2)$$

In the present invention, time (T)required until the change ratio (Rn) falls in a range of 95% to 105%(100%±5%) in at least two successive measurements is sets a mixability index. In other words, when Rn and Rn+1 successively fall in the range of 95% to 105% for the first time, the time (T) until the nth measurement becomes the index.

It has been observed that a mixture whose Rn becomes 95%<R<105% is actually homogeneous in its external appearance and a mixture whose Rn does not fall in the range of 100%±5% is not homogeneous in visual observation.

The cosmetic kit of the present invention includes a plurality of cosmetic bases, and the above time (T) measured when at least two types of the cosmetic bases are mixed is within 35 minutes and preferably within 30 minutes. Cosmetic bases prepared to satisfy such a condition may be mixed by the user easily nd without stress.

The above approach, in other words, a determination method of homogenization by using a near-infrared ray measurement may be applied to a determination about mixability of an arbitrary substance other than the cosmetic base in the present invention.

In other words, the determination method may be used as a method of determining mixability of at lot two types of substances, the method in which when the at least two types of substances are contained in the same container, a near-infrared ray measurement of the substances is conducted while the substances are appropriately stirred, a change ratio [(An/An−1)×100] of absorbance (An) to absorbance (An−1) in the previous measurement becomes 9% to 105%, and a change ratio [(An+1/An)×100] to absorbance (An+1) in the next measurement becomes 95% to 105%, the time (T)required until the n−1th measurement is set as an index.

Methods for conducting the stirring may include, for example, stirring such as rotating, vibrating, and shaking a container containing the substances or stirring by a stirrer provided in the container. Substances to be determined are not limited to liquids but may be fluid powders. Further, it is possible to heat the substances in the container simultaneously with stirring, and the mixability of substances that are solid at normal temperature such as thermoplastic substances and w may thereby be determined.

The wavelength range for measuring absorbance is not particularly limited as long as it is a wavelength range of near-infrared rays (750 nm to 2.500 nm).

The time (T) as the "mixability" index may arbitrarily be set according to a required mixing condition. As the mixability between liquid substances, it is possible to set approximately in 60 minutes, 50 minutes, 40 minutes, or 30 minutes, for example, as a threshold of mixability.

In addition to the "mixability", it is preferable for the cosmetic base included in the cosmetic kit of the present invention that the total amount of the customized cosmetics prepared by mixing bases be set to fall in a predetermined range. Specifically, it is based on that the amount of the final customized cosmetics possibly affects the sense of use.

In other words, even if the customized cosmetics are prepared by mixing bases mixable with each other, when the total amount is a amount less the 0.3 mil or exceeding 1.35 ml, the sense of use of the obtained customized cosmetics may lower. The customized cosmetics prepared mainly for the face are preferably made an amount in such a range.

For example, when the above-described information processing system is used, controlling the total amount of the customized cosmetics in a predetermined range may easily be conducted by in advance setting the total amount of the dispensed cosmetic base as in the ninth variation.

As described above, the cosmetic kit of the present invention including a plurality of cosmetic bases, each of the bases having a original feature and being mixable with each other, is particularly suitable for use with a system preparing the customized cosmetic according to the recipe information based on the user-unique information.

The cosmetic base included in the cosmetic kit of the present invention may have forms such as aqueous, oil, oil-in-water type emulsions, water-in-oil type emulsions, and multiple emulsions. Each base includes preferable blended ingredients according to its form. The sense of use of the cosmetics obtained by mixing those bases changes according to the types and amounts (or blending ratio) of the find blended ingredients, and the psychological effect given to the user in application to the skin also changes accordingly. Thus, the customized cosmetic prepared according to the recipe information selected based on the user-unique information functions as a cosmetic suitable for the user on the very day nd at the very time.

In the cosmetic kit of the present invention, each cosmetic base is preferably contained in a separate container and dispensed. Further preferably, each cosmetic base is contained in a cartridge capable of being held by a slot of the cosmetic dispenser and dispensed.

The sense of use of the cosmetic prepared by mixing cosmetic bases may change according to the type of blended thickener. In addition, it is considered that the bases blended with the same thickener we mixable with each other, whereas the bases including different thickeners tend to be les mixable.

However, in the present invention, each base is prepared such that the mixability index (T) falls within 35 minutes by using the determination method using near-infrared rays. Thus, for example, even if different thickeners we blended with a first base and a second base, the customized cosmetic obtained by mixing co provide (the user with) a high usability (excellent texture).

Consequently, the cosmetic kit of the present invention includes a mode in which the cosmetic kit includes a plurality of bases, wherein the first base among the plurality of bases contains a first thickener, the second base contains a second thickener, and the first thickener and the second thickener in which each of the first, second and third thickener is made up of different substances. Such a mode enables the user to have the original sense of use corresponding to each base.

Thickeners blended with bases of the present invention are not particularly limited as long as those are usually used for cosmetics. Examples may include: plant-based polymers such as gum arabic, gum tragacanth, galactan, guar gum, carob gum, gum karaya, gellan gum, carrageenan, and quince seed (marmelo); microbe-based polymers such as xanthan gum, dextran, succino-glucan, and pullulan; animal-based polymers such a collagen, casein, sodium caseinate, albumin, and gelatin; starch-based polymers such as dextrin, sodium alginate, carboxymethyl starch, and methylhydroxypropyl starch; cellulose-based polymers such as methyl cellulose, ethyl cellulose, methylhydroxypropyl cellulose, carboxymethyl cellulose, hydroxyethyl cellulose, hydroxypropyl cellulose, sodium cellulose sulfate, hydroxypropyl cellulose, carbonymethyl cellulose sodium salt, and crystalline cellulose; alginate-based polymers such as sodium alginate and propylene glycol alginate; vinyl-based polymers such as polyvinyl alcohol, polyvinyl acetate, polyvinyl methyl ether, polyvinyl pyrrolidone, copolymers of vinyl pyrrolidone and vinyl acetate, and carboxyvinyl polymer; and acrylic polymers such as sodium polyacrylate, polyethyl acylate, alkanolamine polyacrylate, copolymers of alkyl methacrylate and dimethylaminoethyl methacrylate, poly(2-acrylamido-2-methylpropanesulfonic acid), and poly-methacryloyloxy-trimethylammonimum.

Further, in addition to the thickener, a blended surfactant may affect the sense of use of the base. Consequently, it may be preferable that the combination of a thickener and a surfactant to be blended with each base of the present invention be specified. Surfactants that may be used in the present invention are not particularly limited but may be selected from surfactants raised as example in the following.

Examples of lipophilic nonionic surfactants may include fatty acid esters of sorbitan such as sorbitan monooleate, sorbitan monoisostearte, sorbitan monolaurate, sorbitan monopelmitate, sorbitan monostearate, sorbitan sesquioleate, and diglycerol sorbitan penta-2-ethylhexylate, fatty acid asters of glycerin or polyglycerin such a glycerin monostearate, glycerin oleate-pyroglutanate, and malate esters of glycerin monostemrate, and fatty acid esters of propylene glycol such a propylene glycol monostearate, hydrogenated castor oil derivatives, and glycerin alkyl ether.

Examples of hydrophilic nonionic surfactants may include fatty acid esters of polyoxyethylene sorbitan such as polyoxyethylene sorbitan monooleate and polyoxyethylene sorbitan monostearate, fatty acid esters of polyoxyethylene sorbitan such a polyoxyethylene sorbitan monolaurate, polyoxyethylene sorbitan monooleate, and polyoxyethylene sorbitan monostearate, fatty acid esters of polyoxyethylene glycerin such as polyoxyethylene glycerin monostearate, polyoxyethylene glycerin monoisostearate, and polyoxyethylene glycerin triisostearate, fatty acid esters of polyoxyethylene such as polyoxyethylene monooleate and polyoxyethylene distearate, alkyl ethers of polyoxyethylene such a polyoxyethylene lauryl ether, polyoxyetlhylene oleyl ether, polyoxyethylene stearyl ether, polyoxyethylene (2-octyldodecyl) ether, and polyoxyethylene cholestanol ether, alkylphenyl ethers of polyoxyethylene such as polyoxyethylene octylephenyl ether, polyoxyethylene nonylphenyl oiler, and polyoxyethylene dinonylphenyl ether, a Pluronic type surfactant such as Pluronic, alkyl ethers of polyoxyethylene polyoxypropylene such as (polyoxyethylene polyoxypropylene) cetyl other, (polyoxyethylene polyoxypropylene) 2-decyltetradecyl ether, (polyoxyethylene polyoxypropylene) butyl ether, hydrogenated lanolin, and ethers of polyoxyethylene polyoxypropylene and glycerin, condensation substances of polyethylene or polyoxypropylene and ethylenediamine such as Tetronic, derivatives of polyoxyethylene castor oil or polyoxyethylene hydrogenated castor oil such as polyoxyethylene castor oil, polyoxyethylene hydrogenated castor oil, polyoxyethylene hydrogenated castor oil monoisostearate, polyoxyethylene hydrogenated castor oil triisostearate, polyoxyethylene hydrogenated castor oil monopyroglutamate monoisostearate, and polyoxyathylene hydrogenated castor oil maleate, alkanolamides such a coconut oil fatty acid diethanolamide, lauric acid monoethanolamide, and fatty acid isopropanolamide, fatty acid esters of polyoxyethylene propylene glycol, alkylamines of polyoxyethylene, fatty acid amides of polyoxyethylene, fatty acid esters of sucrose, condensates of polyoxyethylene nonylphenol ad formaldehyde, alkyl ethoxy dimethyl amine oxide, and trioleyl phosphate.

Examples of anionic surfactants may include fatty acid soap such as sodium laurate and sodium palmitate, salts of higher alkyl sulfates such as sodium lauryl sulfate and potassium lauryl sulfate, salts of alkyl ether sulfates such a salts of polyoxyethylene lauryl sulfuric acid and triethanolamine, and sodium polyoxyethylene lauryl sulfate, N-acyl sarcosinates such as sodium lauroyl sarcosinate, sulfonates of higher fatty acid amide such as sodium N-myristoyl-N-methyl taurate, coconut oil fatty acid sodium methyl taurine, and sodium lauryl methyl taurid, phosphate ester salts such as sodium polyoyethylene oleyl ether phosphate and sodium polyoxyethylene stearyl ether phosphate, sulfosuccinates such as sodium di-2-ethylhexylsulfosuccinate, sodium monolauroyl monoethanolamide polyoxyethylene sulfosuccinate, and sodium lauryl polypropylene glycol sulfosuccinate alkyl benzene sulfonates such as sodium dodecylbenzene sulfonate and triethanolamine dodecylbenzene sulfonate, N-acyl glutamates such as monosodium N-lauroyl glutamate and disodium N-stearoyl glutamate, salts of sulfates of higher fatty acid esters such as hydrogenated coconut oil fatty acid glycerin sodium sulfate, carboxylates of polyoxyethylene alkyl ether. α-olefin sulfonate, sulfonates of higher fatty acid esters salts of secondary alcohol sulfuric esters, salts of sulfates of higher fatty acid alkylol amide, sodium lauroyl monoethanolamide succinate, N-palmitoyl aspartic acid, di-, tri-ethanol amine, and hydrolyzed alkaline salts of coconut oil fatty acid collagen.

Examples of cationic surfactants may include alkyl trimethyl ammonium salts such as stearyl trimethyl ammonium chloride and lauryl trimethyl ammonium chloride, dialkyl dimethyl ammonium salts such as distearyl dimethyl ammonium chloride, alkyl pyridinium salts such as poly(N,N'-dimethyl-3,5-methylene piperidinium) chloride and cetylpyridinium chloride, alkyl quaternary ammonium salts, alkyl dimethyl benzyl ammonium salts, alkyl isoquinolinium salts, dialkyl morpholinium salts, polyoxyethylene alkyl amine, alkyl amine salts, fatty acid derivatives of polyamine, fatty acid derivatives of amylalcohol, benzalkonium chloride, benzethonium chloride, cationic polymers, and copolymers of acrylic acid and β-N,N-dimethyl-N-ethyl-ammonioethyl vinylpyrrolidone chloride.

Examples of amphoteric surfactants may include imidazoline-based amphoteric surfactants such as sodium 2-undecyl-N,N,N-tris(hydroxyethyl carboxymethyl)-2-imidazoline and 2-cocoyl-2-imidazolinium hydroxide-1-carboxyethyloxy disodium salt, and betaine-based amphoteric surfactants such as 2-heptadecyl-N-carboxymethyl-N-hydroxyethyl imidazolinium betaine, lauryl dimethyl aminoacetic acid betaine, alkyl betaine, amidobetaine, and sulfobetaine.

Preferable examples of combinations of thickeners and surfactants according to the feature of each base may include the combination of "(ammonium acryloyldimethyltaurte/beheneth-25 methacrylate) crosspolymer" (thickener) and "(acrylates/C10-30 alkyl acylate) crosspolymer" (surfactant), the combination of "Na acrylate/Na acryloyldimethyl taurate) copolymer" (thickener) and "straight-chain polyether modified silicone" (surfactant), and the combination of "carbomer" (thickener) and "polyoxyethylene alkyl ether" (surfactant), but are not limited to those. As the combination of the thickener and the surfactant blended with each of the first base and the second base of the present invention, the first and second bases whose thickeners are different from each other, two types may be selected from the above combination examples, or other combinations may be employed.

Other than the above thickeners and surfactants, the base of the present invention may as needed and appropriately be blended with another ingredient that may usually be used for cosmetics, for example, such as a moisturizing agent, oil (including silicone oil, hydrocarbon oil, and ester oil), an ultraviolet absorber, a sequestrant, a pH adjuster, various kinds of agents, an oxidation inhibitor, a perfume end water based on the feature intended by each base.

Each base is preferably blended with at least one kind of agent such as an antioxidant, an anti-wrinkle agent, a whitening agent, and a rough skin ameliorating agent according to each purpose (intended feature).

Examples of the agents may include L-ascorbic acid and salts of derivatives thereof, tranexamic acid and salts of derivatives thereof, alkoxy salicylic acid and salts of derivatives thereof, and glutathione and salts of derivatives thereof. A more specific description will be made in the following.

Examples of derivatives of L-ascorbic acid may include L-ascorbic acid monoalkyl esters such as L-ascorbic acid monostearate, L-ascorbic acid monopalmitate, and L-ascorbic acid monooleate; L-ascorbic acid monoesters such a L-ascorbic acid monophosphate ester and L-ascorbic acid-2-sulfate ester; L-ascorbic acid dialkyl asters such a L-ascorbic acid distearate, L-ascorbic acid dipalmitate, and L-ascorbic acid dioleate; L-ascorbic acid trialkyl esters such as L-ascorbic acid tristearate, L-ascorbic acid tripalmitate, and L-ascorbic acid trioleate; L-ascorbic acid triesters such as L-ascorbic acid triphosphate ester; and L-ascorbic acid glucosides such as L-ascorbic acid 2-glucoside.

Examples of derivatives of tranexamic acid may include dimers of tranexamic acid (for example, trans-4-(trans-aninomethylcydohexanecarbonyl)aminomethylcyclohexanecarboxylate hydrochloride), esters of tranexamic acid and hydroquinone (for example, 4-(trans-aminonethylcyclohexanecarboxylic acid 4-hydroxyphenyl ester), esters of tranexamic acid and gentisic acid (for example, 2-(trans-4-aminomethylcyclohexyl carbonyloxy)-5-hydroxybenzoic acid), and amide of tranexamic acid (for example, such as trans-4-aminomethyl cyclohexane carboxylic acid methylamide, trans-4-(p-methoxybenzoyl)aminomethylcyclohexanecarboxylic acid, and trans-4-guanidinomethylcyclohexanecarboxylic acid).

Alkoxy salicylic acid is salicylic acid having a hydrogen atom at any of positions 3, 4, and 5 thereof replaced by an alkoxy group or m alkoxy group the substituent is preferably ay of a methoxy group, an ethoxy group, a propoxy group, isoproproxy group, a butoxy group, and an isobutoxy group and further preferably a methoxy group or m ethoxy group. Examples of specific compounds may include 3-methoxysalicylic acid, 3-ethoxysalicylic acid, 4-methoxysalicylic acid, 4-ethoxysalicylic acid, 4-propoxysalicylic acid, 4-isopropoxysalicylic acid, 4-butoxysalicylic acid, 5-methoxysalicylic acid, 5-ethoxysalicylic acid, and 5-propoxysalicylic acid.

Although not particularly limited, the salts of the above agents may include salts such as ammonium salts and amino acid salts in addition to alkaline metal salts or alkaline earth metal salts such a sodium salts, potassium salts, md calcium salts.

Further, examples of the agents may also include: vitamins such as vitamin A derivatives such as vitamin A, vitamin A palmitate, mad vitamin A acetate, vitamin Bs such as vitamin B6 hydrochloride, vitamin B6 tripalmitate, vitamin B6 dioctanoate, vitamin B and derivatives thereof, vitamin B12, and vitamin B15 and derivatives thereof, vitamin Es such as α-tocopherol, β-tocopherol, and vitamin E acetate, vitamin Ds, vitamin H, pentodhenic acid, and pantethin; saponins such as γ-orizanol, allantoin, glycyrrhiic acid (salts), glycyrrhetinic acid, stearyl glycyrrhetinate, hinokitiol, bisabolol, eucalyptone, thymol, inositol, saikosaponin, *ginseng* saponin, luffa saponin, and soapnut saponin; various kinds of agents such as pantothenyl ethyl ether, arbutin, and cepharanthine extracts of plants such as Rumex japonicus, Sophora flavescens, Nuphar japonicum, orange, sage, yarrow, common mallow. Swertia Japonica, thyme, Angelica acutiloba, spruce, birch, field horsetail, sponge gourd, horse-chestnut, saxifrage, Chinese skullcap, arnica, lily, mugwort, Chinese peony, aloe, gardenia, and leaves of cherry blossom, ad pigments such as β-carotene.

EXAMPLES

The present invention is described more specifically in the following by raising examples and the like. The present invention is not limited at all by those examples. Note that the blending amount is denoted by mass percent with respect to the whole amount less otherwise mentioned.

The bases of the prescriptions shown in the following tables 1 to 4 were prepared. Example 1 (table 1) represents a first base, Example 2 (table 2) represents a second base, Example 3 (table 3)represents a third base, and Comparative Example 1 (table 4) represents a fourth base. Those bases were separately contained in four cartridges of the cosmetic dispenser shown in FIG. 4, predetermined amounts were dispensed via the processor, and cosmetics were thereby produced.

TABLE 1

Example 1

| | | |
|---|---|---|
| Water | Water | 65.6 |
| Alcohol | Ethanol | 10 |
| Moisturizing Agent | Glycerin | 5 |
| | BG | 5 |
| | PEG/PPG-17/4 Dimethyl Ether | 5 |
| Thickener | (Ammonium Acryloyldimethyltaurate/Beheneth-25 Methacrylate) Crosspolymer | 1 |
| | PEG-14M | 1 |
| Surfactant | (Acrylates/C10-30 Alkyl Acrylate) Crosspolymer | 0.5 |
| Oil | Dimethicone | 5 |
| | Triethylhexanoin | 1 |
| Neutralizer | Potassium hydroxide | 0.1 |
| Preservative | Phenoxyethanol | 0.5 |
| | Methylparaben | 0.3 |

TABLE 2

Example 2

| | | |
|---|---|---|
| Water | Water | 72.8 |
| Moisturizing Agent | BG | 5 |
| | DPG | 5 |
| | Glycerin | 3 |
| Thickener | Xanthan gum | 0.5 |
| | (Na Acrylate/Na Acryloyldimethyltaurate) Copolymer | 1 |
| Surfactant | (Acrylates/C10-30 Alkyl Acrylate) Crosspolymer | 0.2 |
| | Sorbitan Oleate | 0.2 |
| | Polysorbate 80 | 0.2 |
| | Sucrose Stearate | 0.5 |
| | PEG-10 Dimethicone | 0.5 |
| Oil | Dimethicone | 5 |
| | Pentaerythrtyl Tetraethyl Hexanoate | 3 |
| | Glyceryl Diisostearate | 1 |
| | Isohexadecane | 1 |
| | Hydrogenated Polydecene | 0.5 |
| Neutralizer | Potassium hydroxide | 0.1 |
| Preservative | Phenoxyethanol | 0.5 |

TABLE 3

Example 3

| | | |
|---|---|---|
| Water | Water | 75.4 |
| Alcohol | Ethanol | 10 |
| Moisturizing Agent | DPG | 5 |
| | Glycerin | 5 |
| | PEG/PPG-14/7 Dimethyl Ether | 3 |
| Thickener | Carbomer | 0.5 |
| Surfactant | PPG-13 Decyltetradeceth-24 | 0.5 |
| Neutralizer | Potassium hydroxide | 0.1 |
| Preservative | Phenoxyethanol | 0.5 |

TABLE 4

Comparative Example 1

| | | |
|---|---|---|
| Water | Water | 24 |
| Moisturizing Agent | Glycerin | 15 |
| | BG | 10 |
| | PEG-150 | 5 |
| Thickener | (Al/Mg) Silicate | 1 |
| Surfactant | PEG-10 Dimethicone | 4 |
| | Distearyldimonium Chloride | 0.5 |

TABLE 4-continued

Comparative Example 1

| | | |
|---|---|---|
| Oil | Cyclopentasiloxane | 30 |
| | Hydrogenated Polydecene | 5 |
| | Cetyl Ethylhexanoate | 5 |
| Preservative | Phenoxyethanol | 0.5 |

The mixability (time required for homogenization; T) in the case that the bases of Example 1 to Example 3 nd Comparative Example 1 were used and mixed at the ratios shown in the following table 5 such that the total amount becomes 8 g was measured by the method described in the paragraphs above, and expert panelists evaluated the sense of use (heaviness in spreading, quickness of penetration, and stickiness) of the obtained mixtures (customized cosmetics).

Evaluation criteria of the sense of use were as follows:

A: Four or more among eight expert panelists evaluate that the sense of use is excellent.

B: Three or less among eight expert panelists evaluate that the sense of use is excellent.

TABLE 5

| | Sample 1 | Sample 2 | Sample 3 |
|---|---|---|---|
| Bases | Example 1:Example 2 = 1:1 | Example 1:Example 2:Example 3 = 2:3:2 | Example 2:Comparative Example 1 = 1:1 |
| Homogenization Time | 10 min | 35 min | 120 min or longer |
| Usability | A | A | B |

As shown in table 5, when the bases we mixable with each other and the time (T) required for homogenization, which is measured by the method described in the paragraphs 0180 to 0184, is within 35 minutes, the cosmetic obtained by mixing has high usability. On the other hand, as for the sample 3 of the combination of less mixable buss (the time required for homogenization is 120 minutes), the obtained cosmetic has insufficient usability.

When the cosmetic was prepared by mixing the bases, the change in usability according to the total amount was observed. The results are shown in table 6.

The bases of Example 1, Example 2, and Example 3 were used a the bases to be mixed, and two or three bass selected from those were mixed at a plurality of ratios. The same usability was exhibited if the total amount was the same. In other words, particularly for cosmetics for the face, it is preferable to set the total amount range (a range of 0.3 to 1.35 ml) with which high usability has been observed.

TABLE 6

| | Sample a | Sample b | Sample c | Sample d | Sample e |
|---|---|---|---|---|---|
| Total Amount of Bases | 0.3 ml | 0.9 ml | 1.05 ml | 1.2 ml | 1.35 ml |
| Usability After Mixing | A | A | A | A | A |

An example of the formulation of cosmetic bases suitable for use of the kit of the present invention is shown below.

TABLE 7

| | |
|---|---|
| Water | Balance |
| DPG | 10.00% |
| BG | 5.00% |
| Glycerin | 3.00% |
| PEG/PPG-14/7 Dimethyl Ether | 1.00% |
| Betain | 1.00% |
| Phenoxyethanol | 0.50% |
| PEG/Polybutylene Glycol-44/15 Methyl Ether | 0.30% |
| Hydrogenated Dimer Dilinoleyl (PEG-240/Decyltetradeceth-20/HDI) Copolymer | 0.30% |
| Chinese Skullcap Root Extract | 0.10% |
| Carbomer | 0.12% |
| Potassium hydroxide | 0.10% |
| Hypericum Flower/Leaf/Stem Extract | 10.00% |
| EDTA-2Na | q.s. |
| Na Pyrosulfite | q.s. |
| Blue No. 1 | q.s. |
| Red No. 227 | q.s. |
| Total | 100 |

1 Information processing system
10 Client apparatus
11 Memory
12 Processor
13 I/O interface
14 Communication interface
15 GPS module
16 Camera
30 Server
31 Memory
32 Processor
33 input and output interface
34 Communication interface
50 Cosmetic dispenser
51 Memory
52 Processor
53 I/O interface
54 Communication interface
55 Mixer
56 Heater
70 Predictive information providing server
90 Wearable device

The invention claimed is:

1. A method, for preparation of a cosmetic kit suitable for use in a preparation of a customized cosmetic which is prepared by mixing plurality of cosmetic bases in accordance with a recipe information determined based on user-unique information, wherein:

said cosmetic kit comprise a plurality of cosmetic bases; and said method comprises the steps of:

(a) rotating, at a predetermined speed, a container containing at least two cosmetic bases selected from said plurality of cosmetic bases;

(b) obtaining, at predetermined time internals, a series of reflected near-infrared integrated absorbance measurements of said at least two selected cosmetic bases in said rotating container;

(c) calculating, for each absorbance measurement, a change ratio Rn between the absorbance in an (n)th measurement ($A_n$) and the absorbance in the subsequent (n+1)th measurement ($A_{n+1}$), said ratio $R_n$ being $R_n = 100 \times (A_{n+1})/(A_n)$:

(d) determining the elapsed time (T), measured from the initiation of rotation at step (a), at which a calculated value of Rn is between 95% and 105% of the preceding value of $R_n$;

(e) determining said plurality of cosmetic bases to comprise at least two selected cosmetic bases having said elapsed time T of 35 minutes or less; and (f) filling each of said plurality of cosmetic bases determined in step (e) into an individual cartridge.

2. The method, according to claim 1, wherein: said plurality of cosmetic base are selected based in accordance with said recipe information.

3. The method, according to claim 1, wherein: said user-unique information comprises: at least one selected from the group consisting of user attribute information related to the user's attributes, environmental information related to the user's environment, action information related to the user's action, psychosomatic information related to the user's psychosomatic state, skin information related to the use's skin, and information related to cosmetics that the user has used.

4. The method, according to claim 2, wherein: said recipe information comprises at least one selected from the group consisting of a usage amount, a blending ratio, and a total amount of respective cosmetic bases.

5. The method, according to claim 1, wherein: each of said individual cartridges is adapted for use in a cosmetic dispenser comprising:

a plurality of cartridge slots configured to detachably hold said cartridges containing said cosmetic bases; and a dispense port for dispensing the respective cosmetic bases based on said recipe information.

6. The method, according to claim 5, wherein: said cosmetic dispenser is communicably connected with an information processing apparatus capable of processing said user-unique information and transmitting said recipe information to said cosmetic dispenser.

* * * * *